US010172969B2

(12) United States Patent
Nakamoto et al.

(10) Patent No.: US 10,172,969 B2
(45) Date of Patent: Jan. 8, 2019

(54) CLOTHES TREATING DEVICE

(71) Applicants: AQUA CO., LTD., Tokyo (JP);
Qingdao Haier Washing Machine Co., Ltd., Shandong (CN)

(72) Inventors: Shigeharu Nakamoto, Tokyo (JP);
Hazime Suzuki, Tokyo (JP); Takayuki Nagai, Tokyo (JP); Tomohiro Yamauchi, Tokyo (JP)

(73) Assignees: Aqua Co., Ltd. (JP); Qingdao Haier Washing Machine Co., Ltd. (CN)

( * ) Notice: Subject to any disclaimer, the term of this patent is extended or adjusted under 35 U.S.C. 154(b) by 0 days.

(21) Appl. No.: 15/572,988

(22) PCT Filed: May 13, 2016

(86) PCT No.: PCT/CN2016/082112
§ 371 (c)(1),
(2) Date: Nov. 9, 2017

(87) PCT Pub. No.: WO2016/180373
PCT Pub. Date: Nov. 17, 2016

(65) Prior Publication Data
US 2018/0117204 A1 May 3, 2018

(30) Foreign Application Priority Data

May 13, 2015 (JP) ................. 2015-098505

(51) Int. Cl.
*A61L 9/12* (2006.01)
*D06F 73/02* (2006.01)

(52) U.S. Cl.
CPC ............. *A61L 9/12* (2013.01); *D06F 73/02* (2013.01); *A61L 2209/13* (2013.01); *A61L 2209/15* (2013.01)

(58) Field of Classification Search
CPC .... A61L 9/12; A61L 2209/13; A61L 2209/15; D06F 73/02
See application file for complete search history.

(56) References Cited

U.S. PATENT DOCUMENTS 6,134,806 A  10/2000 Dhaemers
8,038,963 B1  10/2011 Chen

FOREIGN PATENT DOCUMENTS

EP         1057923 A1   12/2000
JP      2006149822 A    6/2006

*Primary Examiner* — Sean E Conley
(74) *Attorney, Agent, or Firm* — Burns & Levinson, LLP; Joseph M. Maraia

(57) ABSTRACT

Disclosed is a clothes treating device. A clothes deodorizing device includes: a bag body for accommodating clothes; an ozone supply device to supply air with ozone into the bag body; an exhaust part arranged on the bag body and used for air exhausted outside the bag body to pass through; and an ozone removing filter arranged on the exhaust part and used for removing ozone in air passing through the exhaust part. The exhaust part is formed by material harder than material forming the bag body and is installed on a first opening part formed in the bag body.

4 Claims, 21 Drawing Sheets

CLOTHES TREATING DEVICE

CROSS REFERENCE TO RELATED APPLICATIONS

This application is the U.S. national phase entry under 35 U.S.C. § 371 of International Application No. PCT/CN2016/082112, filed May 13, 2016, entitled CLOTHES TREATING DEVICE, which claims priority to Japanese Patent Application No. 2015-098505, filed May 13, 2015, the contents of which are incorporated herein by reference in their entirety for all purposes.

TECHNICAL FIELD

The present disclosure relates to a clothes treating device for implementing treatment, such as deodorization, on clothes.

BACKGROUND

In the past, a clothes renovating device is known. The clothes renovating device includes a storage warehouse capable of hanging clothes on a hanging rod for storage, and introduces circulating air absorbing clothes smell into an ozone deodorizer by enabling high-temperature and high-humidity air to perform internal circulation in the storage warehouse, thereby deodorizing the clothes (with reference to a patent literature 1).

Since the clothes renovating device includes a storage warehouse, an device body is easy to become larger. Therefore, a clothes treating device, including a bag body for accommodating clothes and an ozone supply device for supplying air with ozone into the bag body and capable of implementing treatment, such as deodorization, on clothes accommodated in the bag body through ozone, in a manner of easy installation at home without large installation space is considered to be realized.

EXISTING TECHNICAL LITERATURE

Patent Literature

Patent Literature 1: Japan specifically disclosed No. 04-327900 Bulletin

SUMMARY

Problems to be Solved by the Disclosure

In the clothes treating device, ideally, air is exhausted from a bag body after an ozone concentration in the air is reduced as much as possible.

The present disclosure is a technical solution completed in view of the problem. A purpose of the present disclosure is to provide a clothes treating device capable of exhausting air from the bag body after reducing the ozone concentration in the air.

Solution for Solving the Problems

A clothes treating device in a main embodiment of the present disclosure includes: a bag body for accommodating clothes; an ozone supply device to supply air with ozone into the bag body; an exhaust part arranged on the bag body and used for air exhausted outside the bag body to pass through; and an ozone removing filter arranged on the exhaust part and used for removing ozone in air passing through the exhaust part.

Through the above structure, the ozone in the air is removed through the ozone removing filter when the air beneficial for clothes deodorization is exhausted through the exhaust part. Thus, the air after the ozone concentration is reduced may be exhausted from the bag body.

In the clothes treating device in the present embodiment, the exhaust part is installed on an opening part formed in the bag body, and is composed of a first member installed on the opening part from outer side of the bag body and a second member installed on the opening part from inner side of the bag body. In this case, the first member has a first flange part covering periphery of the opening part from outer side, and the second member has a second flange part covering periphery of the opening part from inner side. Moreover, the exhaust part is assembled by combining the first member and the second member in a manner of clamping the bag body from inner side and outer side.

When such a structure is adopted, if the exhaust part is installed on the opening part, periphery of the opening part is sealed by the first flange part and the second flange part. Therefore, the air with the ozone in the bag body is difficult to leak from the opening part.

When the above structure is adopted, then a guide part, which is to be inserted into the opening part when one member of the first member and the second member is installed on the opening part, is formed on the one member of the first member and the second member.

When such a structure is adopted, one of the members is easy to be installed on the bag body and assembly of the exhaust part becomes easy.

The clothes treating device in the present embodiment may adopt a structure that a clothes rack retention part, for retaining a clothes rack for clothes to hang clothes in the bag body, is integrally formed with the exhaust part.

Through the above structure, the exhaust part and the clothes rack retention part are installed on the bag body in one step.

The clothes treating device in the present embodiment may further include a bag body retention part for retaining the bag body above the ozone supply device. In this case, an installation part, installed on the bag body retention part, is integrally formed with the exhaust part.

Through the above structure, the exhaust part and the installation part may be installed on the bag body in one step.

Effects of the Disclosure

Through the present disclosure, a clothes treating device capable of exhausting the air from the bag body after reducing the ozone concentration in the air may be provided.

Effects and significance of the present disclosure may be further clarified by describing embodiments shown below. However, the following embodiments are just illustration during implementation of the present disclosure. The present disclosure is not limited by disclosure in the following embodiments.

DETAILED DESCRIPTION

A clothes deodorizing device in an embodiment of a clothes treating device of the present disclosure is described below with reference to drawings.

Figure 1:
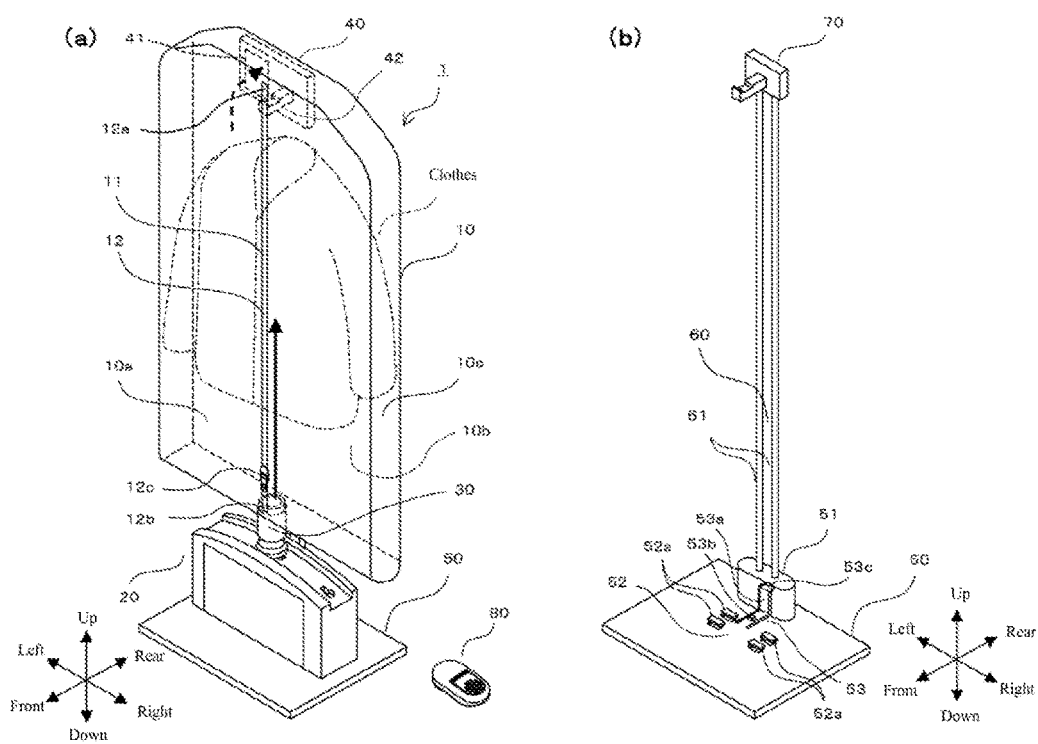
FIG. 1 is a structural diagram illustrating a clothes deodorizing device involved in embodiments.

FIG. 1 is a structural diagram illustrating a clothes deodorizing device 1. FIG. 1(a) is a three-dimensional diagram illustrating a clothes deodorizing device 1. FIG. 1(b) is a three-dimensional diagram illustrating a base 50, a supporting column 60 and a bag body retention part 70 that form a clothes deodorizing device 1.

By referring to FIG. 1, the clothes deodorizing device 1 includes: a bag body 10, an ozone supply device 20, an induction pope 30, an exhaust and clothes rack retention unit 40, a base 50, a supporting column 60, a bag body retention part 70 and a fragrance supply unit 80.

The bag body 10 accommodates various clothes such as western-style clothes, coats and the like. The bag body 10 is formed in a manner of overlapping a plurality of fabrics without air permeability so that tightness is adequate. The bag body 10 has an approximately lengthwise rectangular shape with flat front and rear, and is made of a front fabric 10a forming a front surface, a rear fabric 10b forming a rear surface and side fabrics 10c forming an upper, a lower, a left and a right side surfaces.

An up-down size of the bag body 10 is set as a size capable of accommodating long shirts, long coats and other long clothes. In addition, a front-rear size of the bag body 10 is set as a size capable of accommodating one piece of clothes. It should be noted that the up-down size of the bag body 10 may also be set as a size incapable of accommodating long clothes, and the front-rear size may also be set as a size capable of accommodating about two or three pieces of clothes arranged in front and behind.

In the front surface of the bag body 10, in an approximate center of a left-right direction, a gap that forms a throwing inlet of the clothes is formed from an upper end to a lower end. A zipper 12 is installed at the throwing inlet 11. A starting end part 12a and an end part 12b when the zipper 12 performs locking are respectively located on an upper end and a lower end of the bag body 10. A slider 12c of the zipper 12 moves between the starting end part 12a and the end part 12b. When the slider 12c is pulled downwards from the starting end part 12a, the zipper 12 is closed so that the throwing inlet 11 is locked; and when the slider 12c is pulled upwards from the end part 12b, the zipper 12 is opened so that the throwing inlet 11 is opened. In this way, since a pull-down direction of the slider 12c is set as a locking direction of the throwing inlet 11, in a locking state of the throwing inlet 11, self-weight of the slider 12c acts in the locking direction. Therefore, different from a case that a pull-up direction of the slider 12c forms the locking direction of the throwing inlet 11, a hidden danger that the end part 12b, i.e., a closed part of the zipper 12, is opened due to the self-weight of the slider 12c does not exist.

The ozone supply device 20 performs deodorization operation for deodorizing the clothes and fragrance increasing operation for increasing fragrance on the clothes. During deodorization operation, the ozone supply device 20 performs an action of enabling exhausted air to contain ozone to supply air with the ozone to the bag body 10. In addition, when the ozone supply device 20 performs fragrance increasing operation, the ozone supply device 20 performs an action of enabling the exhausted air not to contain the ozone to supply air without the ozone to the bag body 10.

The induction pipe 30 is connected with the bag body 10 and the ozone supply device 20. The air exhausted from the ozone supply device 20 is guided into the bag body 10. During deodorization operation, air with the ozone passes through the introduction pipe 30; and during fragrance increasing operation, air without the ozone passes through the introduction pipe 30.

An exhaust and clothes rack retention unit 40 is arranged on an upper part of a rear surface of the bag body 10. The exhaust and clothes rack retention unit 40 integrally forms an exhaust part 41 having an ozone removing function and a clothes rack retention part 42 for retaining a clothes rack for clothes to hang clothes through resin material. The air with the ozone beneficial for clothes deodorization is exhausted through the exhaust part 41 from the bag body 10 to outer side of the bag body 10. When the air passes through the exhaust part 41, the ozone included in the air is removed.

The base 50 is a flat plate with a specified shape, such as a quadrangle. The ozone supply device 20 is carried on the base 50. A supporting part 51 for supporting the supporting column 60 is formed at a rear of the base 50. Moreover, a first fixing part 52 and a second fixing part 53 for fixing the ozone supply device 20 in a manner of enabling the front surface of the ozone supply device 20 to face a direction of the front surface of the base 50 are formed on the base 50. The first fixing part 52 is composed of a plurality of hooked claw parts 52a. The second fixing part 53 includes: an L-shaped elastic rod 53a with one end part supported by the base 50, a bulge 53b formed near the rear slightly relative to one end part of the elastic rod 53a, and a pressing part 53c formed on the other end part of the elastic rod 53a. When the pressing part 53c is pressed downwards, the elastic rod 53a generates elastic deformation and the bulge 53b is contracted into the lower part.

The supporting column 60 is composed of two rods 61. A lower end part of the supporting column 60 is installed on the supporting part 51, and is erect relative to the base 50. The supporting column 60 may be not composed of two rods 61, but composed of one or more than three rods. In addition, a telescopic mechanism capable of adjusting the height of the supporting column 60 may further be arranged on the supporting column 60.

A bag body retention part 70 is installed at an upper end of the supporting column 60. The bag body retention part 70 hangs and retains the bag body 10 in such a manner that the bag body 10 cannot move in any direction of front and rear, up and down and left and right.

The fragrance supply unit 80 is used when fragrance increasing operation is performed through the ozone supply device 20. The fragrance supply unit 80 is detachably installed on the induction pipe 30, so that air supplied to the bag body 10 contains fragrant ingredients.

Next, structures of the bag body 10 and the introduction pipe 30 and the exhaust and clothes rack retention unit 40 which are installed in the bag body 10 are described in detail.

Figure 2:
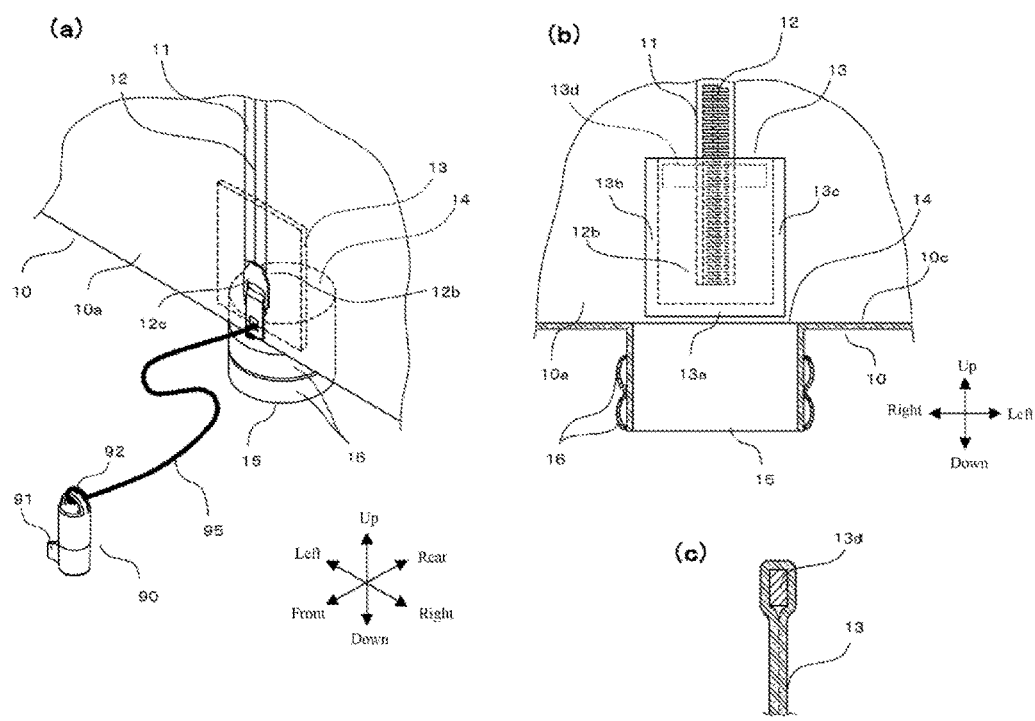
FIG. 2 is a diagram illustrating a lower central part of a bag body involved in embodiments.
Figure 3:
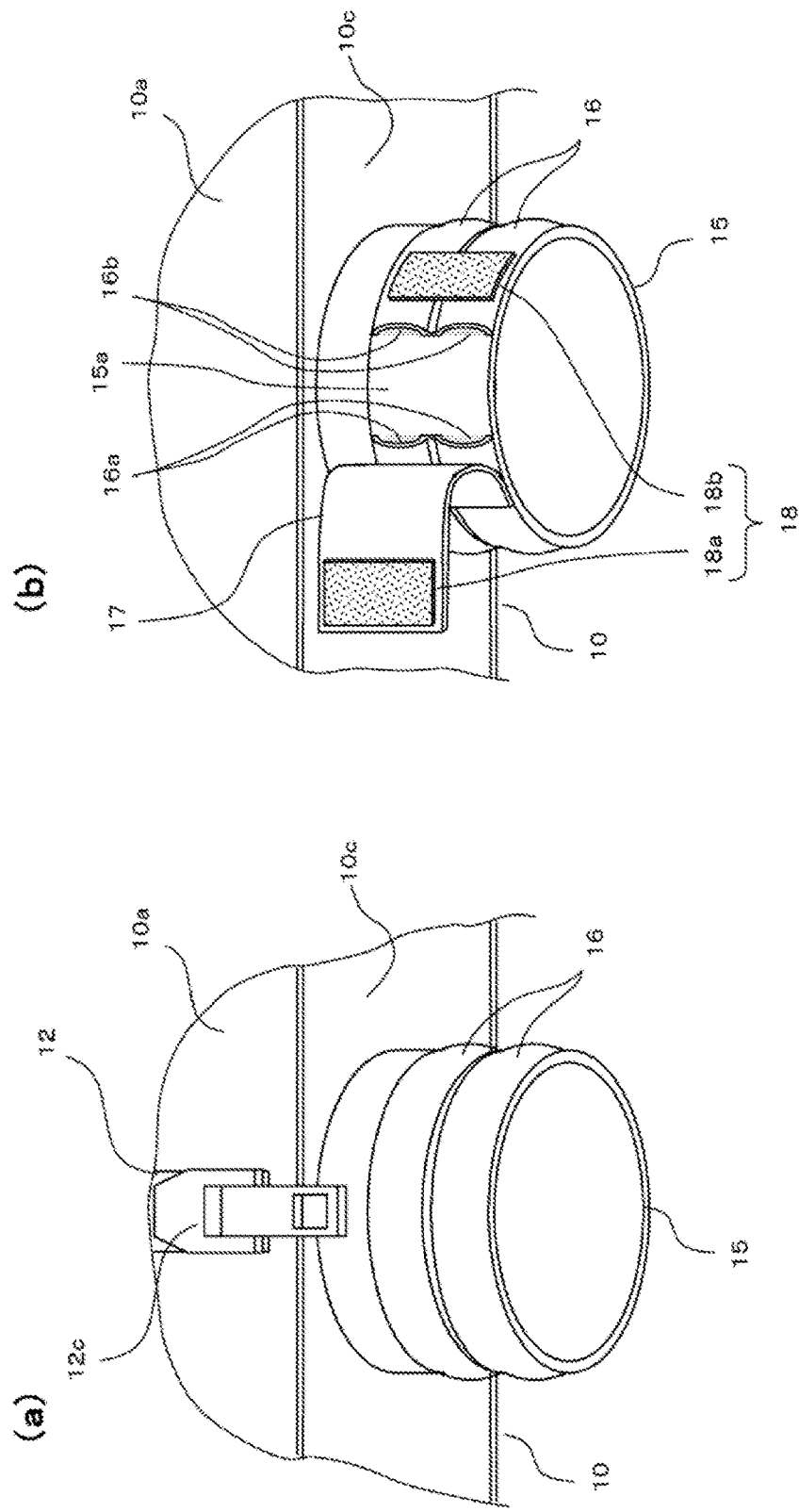
FIG. 3 is a diagram illustrating a lower central part of a bag body involved in embodiments.

FIG. 2 and FIG. 3 are diagrams illustrating a lower central part of a bag body 10. FIG. 2(a) is a front three-dimensional diagram, and FIG. 2(b) is a rear section view. FIG. 3(a) is a three-dimensional diagram during observation from a front lower part. FIG. 3(b) is a three-dimensional diagram during observation from a rear lower part. FIG. 3(d) shows a side section of an upper part of an end hood 13.

At an inner surface of the front fabric 10a of the bag body 10, the end hood 13 is installed in a manner of covering the end part 12b of the zipper 12, i.e., the closed part, from inner side of the bag body 10. The end hood 13 has a rectangle formed by fabrics without air permeability, and a lower edge part 13a, a right edge part 13b and a left edge part 13c are tightly fixed to the inner surface of the front fabric 10a through a fixing method such as sewing, bonding and the like.

When the zipper 12 is not adequately closed to the end, the closed part of the zipper 12 is easy to become a slightly open state. As mentioned above, periphery of the closed part is covered by the end hood. During deodorization operation, since the air is introduced into the bag body 10, pressure in the bag body 10 is increased; and since the pressure is increased, the end hood 13 is pushed to the front surface side of the bag body 10 and is easy to become a state close to the inner surface of the front fabric 10a. Therefore, even if the closed part of the zipper 12 is slightly opened, the air with the ozone is difficult to leak from the closed part.

It should be noted that at an upper end part of the end hood 13, filling material 13d made of polyurethane rubber and the like is accommodated in the end hood 13 in a manner that thickness gets bigger. Thus, the zipper 12 can be prevented from being engaged to the upper end part of the end hood 13 when the zipper 12 is closed.

To detect the locking of the throwing inlet 11 through the zipper 12, a detection lock 90 is connected with the slider 12c, and more specifically with a handle of the slider 12c through a connecting rope 95. The detection lock 90 has a cylindrical shape. A protruding part 91 is formed at a lower end part of a circumferential surface of the detection lock 90, and a hanging ring part 92 for fixing the connecting rope 95 is formed at an upper end part. One end part of the connecting rope 95 is connected with the handle of the slider 12c, and the other end part is connected with the hanging ring part 92. The connecting rope 95 may be a rope with a predetermined length, and for example, is realized by a silk ribbon, a chain, a metal wire and the like.

On the bag body 10, an air inlet 14 is formed in the central part of a lower surface and a cylindrical part 15 droops from the inlet 14. The cylindrical part 15 encircles a top end part of the introduction pipe 30 inserted into the inlet 14. The top end part of the introduction pipe 30 is fixed to the cylindrical part 15.

On an outer circumferential surface of the cylindrical part 15, approximately circular belt penetrating parts 16 are arranged in a vertical parallel mode along a circumferential direction. Both end parts of each belt penetrating part 16 are opened at a rear surface part 15a of the cylindrical part 15 at the rear surface side forming the bag body 10. Each belt penetrating part 16 is used for the following bundle belt to penetrate through.

On an outer circumferential surface of the cylindrical part 15, to shield a rear surface part 15a, a belt-shaped shielding part 17 is further arranged. One end side of the shielding part 17 is installed near an open end 16a at one side of upper and lower belt penetrating parts 16. A surface of one side of a hook & loop 18, such as a hook surface 18a, is formed on the other end side of the shielding part 17; and a surface of the other side of the hook & loop 18, such as a loop surface 18b, is formed near an open end 16b at the other side of upper and lower belt penetrating parts 16.

Figure 4:
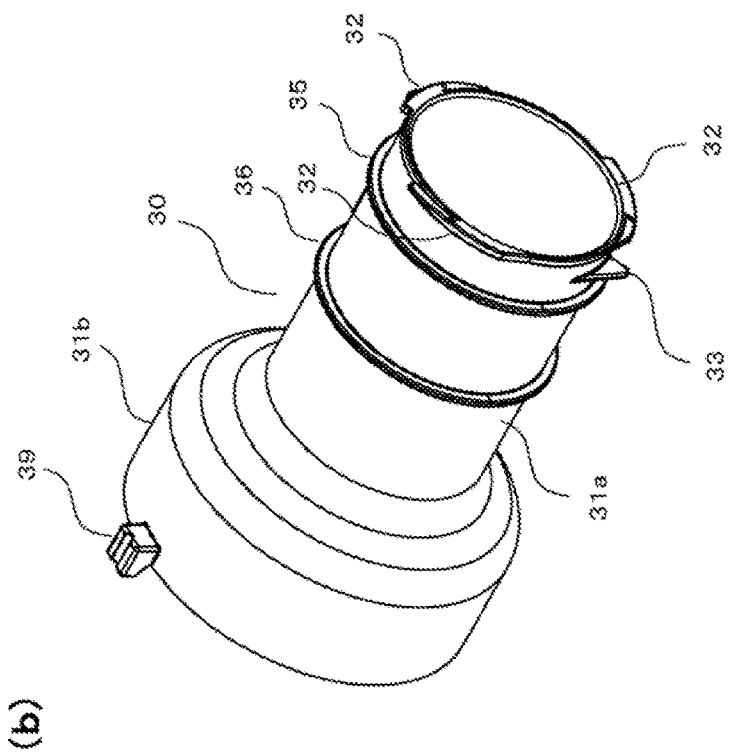
FIG. 4 is a structural diagram illustrating an induction pipe involved in embodiments.
Figure 4:
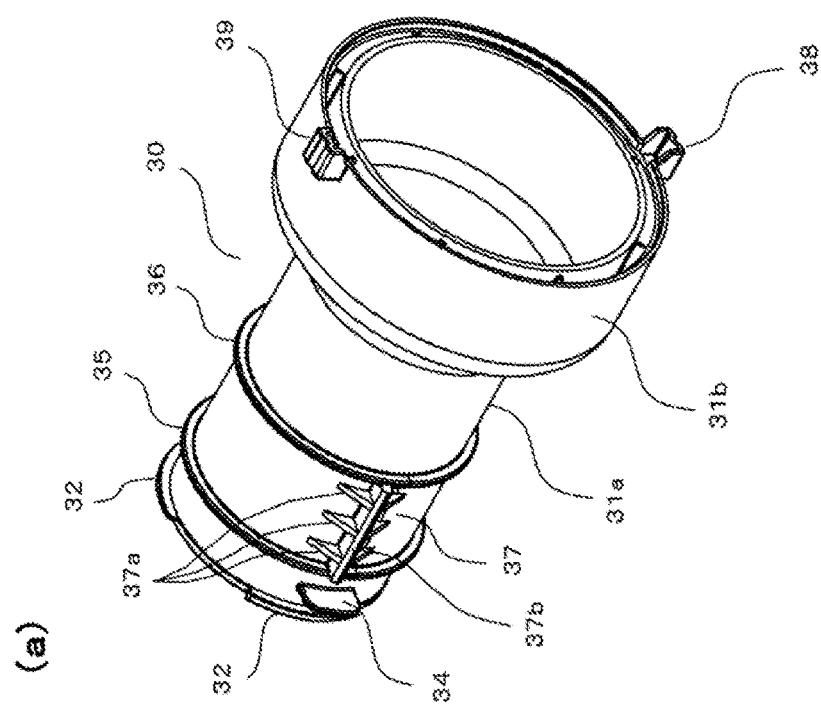

FIG. 4 is a structural diagram illustrating an induction pipe 30. FIG. 4(a) is a three-dimensional diagram during observation from a lower end side. FIG. 4(b) is a three-dimensional diagram during observation from an upper end side.

The induction pipe 30 includes a cylindrical main part 31a with a relatively small outer diameter and a cylindrical connecting part 32b formed under the main part 31a and having a relatively large outer diameter. A boundary part between the main part 31a and the connecting part 32b has a shape that outlines are gradually centralized together.

A plurality of clamping pieces 32 for fixing the fragrance supply unit 80 are formed at an upper end of the main part 31a. In a position slightly lower than the clamping pieces 32 of the main part 31a and in positions that the introduction pipe 30 faces a front side and a rear side of the bag body 10 in a state of being installed on the bag body 10, a front flange part 33 and a rear flange part 34 are formed. In a position slightly lower than the flange parts 33 and 34 of the main part 31a, annular upper flange part 35 and lower flange part 36 are formed at a specified interval along an up-down direction. A protruding strip 37 that vertically extends is formed between the upper flange part 35 and the lower flange part 36 and in a position of facing the rear of the bag body 10 in a state of installation on the bag body 10. The protruding strip 37 is formed in a shape approximate to a triangular prism through triangular ribs 37a vertically parallel and longitudinal ribs 37b for connecting the triangular ribs 37a.

A right claw part 38 and a left claw part 39 are respectively formed at a lower end of the connecting part 31b and in a position facing a right side of the bag body 10 and in a position facing a left side in a state of installation on the bag body 10.

Figure 5:
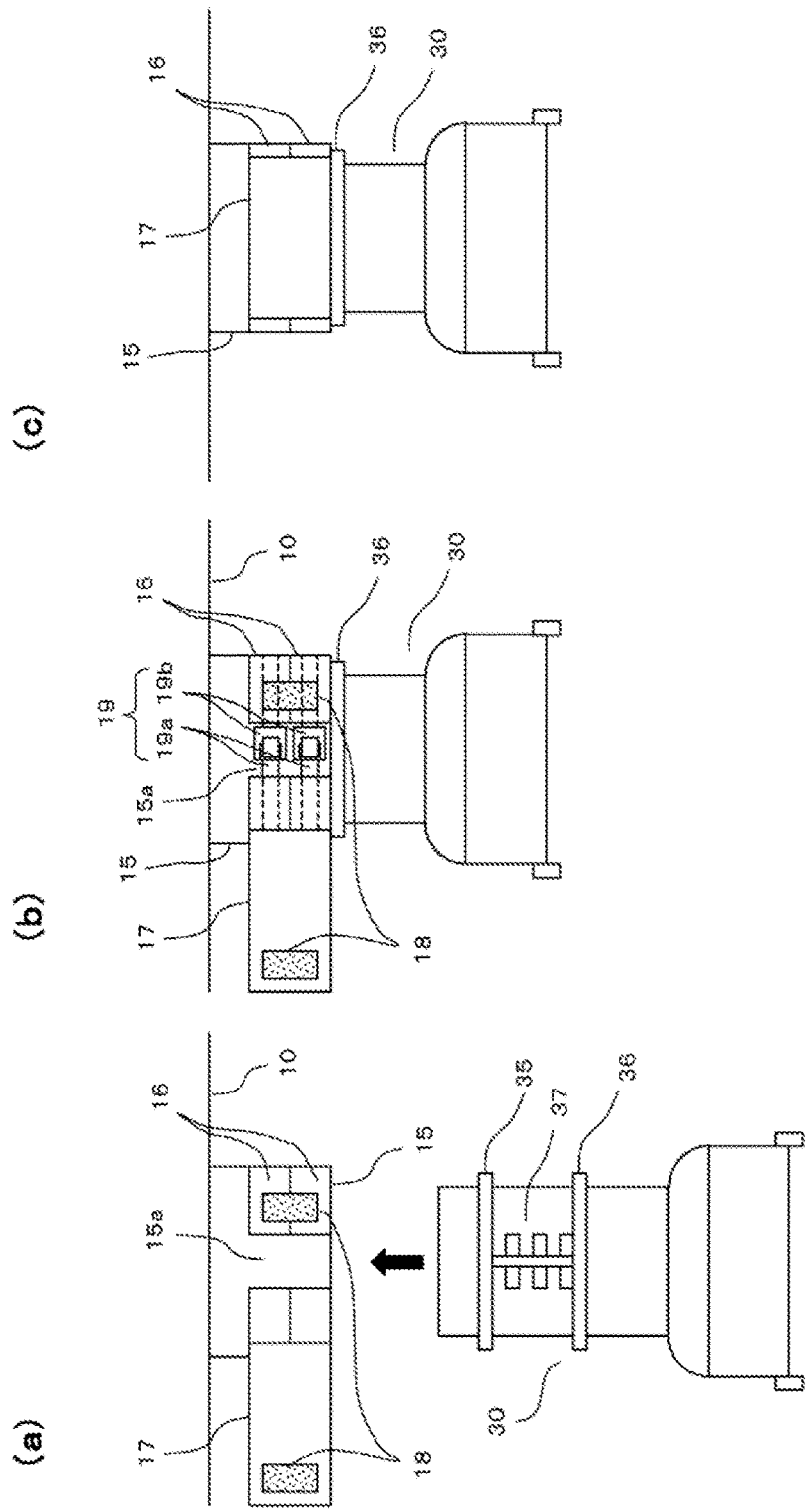
FIG. 5 is a schematic diagram illustrating a flow that an induction pipe is installed on a bag body involved in embodiments.

FIG. 5 is a schematic diagram illustrating a flow that an induction pipe 30 is installed on a bag body 10.

As shown in FIGS. 5(a) and (b), the introduction pipe 30 is inserted into a position close to the lower flange part 36 in the cylindrical part 15 in an orientation that the protruding strip part 37 is located on the rear surface part 15a. As shown in FIG. 5(b), a bundling belt 19 is inserted into a belt penetrating part 16, and the bundling belt 19 is wound on the cylindrical part 15. The bundling belt 19 is composed of a head 19a and a belt part 19b. At a rear surface part 15a, the belt part 19b penetrates through the head 19a, and fastens the cylindrical part 15 to inner side through the bundling belt 19. An excessive part of the belt part 19b is cut off. Then, as shown in FIG. 5(c), the other end side of the shielding part 17 is fixed to the belt penetrating part 16 through a hook & loop 18. The head 19a is shielded by the shielding part 17. In this way, installation of the introduction pipe 30 on the bag body 10 is completed.

Figure 6:
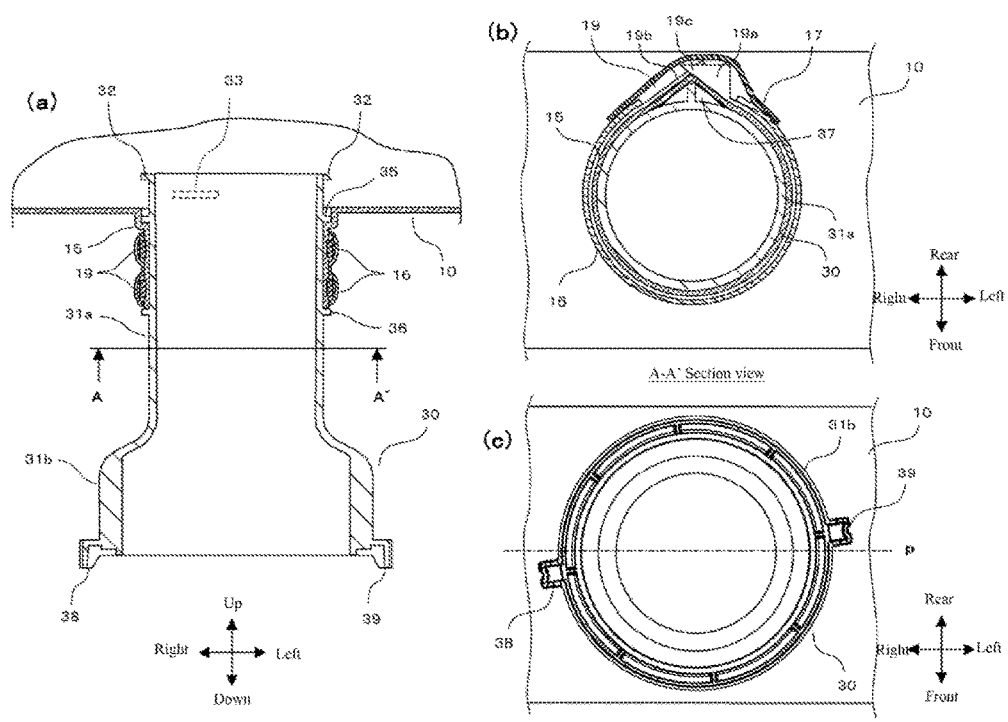
FIG. 6 is a diagram illustrating a lower central part of a bag body in a state of installing an induction pipe involved in embodiments.

FIG. 6 is a diagram illustrating a lower central part of a bag body 10 in a state of installing an induction pipe 30. FIG. 6(a) is a rear section view illustrating a lower central part of a bag body 10. FIG. 6(b) is an A-A' section view of FIG. 6(a). FIG. 6(c) is a diagram during observation of a lower central part of a bag body 10 from a lower side.

As shown in FIG. 6(a), in a state that the introduction pipe 30 is installed on the cylindrical part 15 of the bag body 10, the upper and the lower flange parts 35 and 36 and the bundling belt 19 are clamped along the up-down direction, so that the introduction pipe 30 is fixed to the cylindrical part 15 along the up-down direction. Namely, the introduction pipe 30 passes through the lower flange part 36, and does not move upwards or enter the bag body 10; and passes through the upper flange part 35, and does not move downwards or separate from the bag body 10. Moreover, as shown in FIG. 6(b), a combining part 19c of the head 19a and the belt part 19b of the bundling belt 19 is clamped with the protruding strip part 37 of the introduction pipe 30 along the circumferential direction. Thus, the introduction pipe 30 is fixed to the cylindrical part 15 along the circumferential direction. In this way, the introduction pipe 30 is installed in a manner of not separating from the bag body 10 and also not rotating relative to the bag body 10. In addition, the right claw part 38 and the left claw part 39 of the introduction pipe 30 present a predetermined position relationship relative to the bag body 10. Namely, as shown in FIG. 6(c), the right claw part 38 is in a position slightly forward than a center line P of the front-rear direction of the bag body 10, and the left claw part 39 is in a position slightly backward than the center line P of the front-rear direction of the bag body 10.

As shown in FIG. 6(a), the top part of the introduction pipe 30 is protruded in a manner of being closer to the upper part than the lower surface of the bag body 10. The front flange part 33 and the rear flange part 34 are in positions slightly close to the upper part than the lower surface of the bag body 10.

Figure 7:
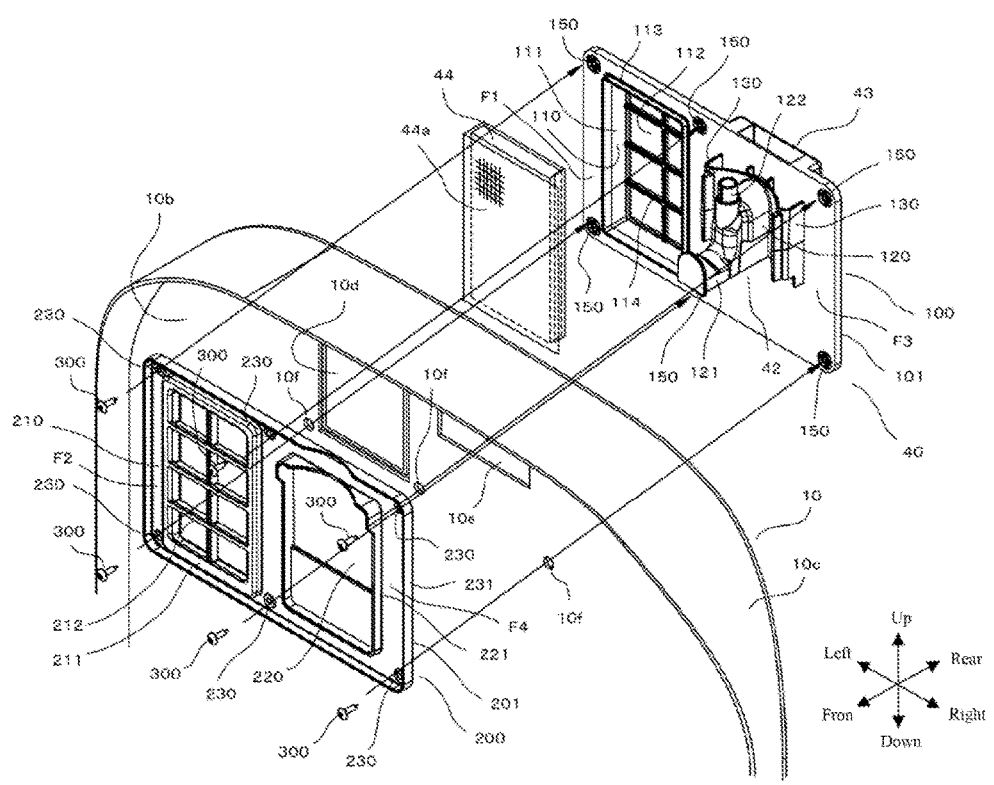
FIG. 7 is a structural diagram illustrating an exhaust and clothes rack retention unit involved in embodiments.
Figure 8:
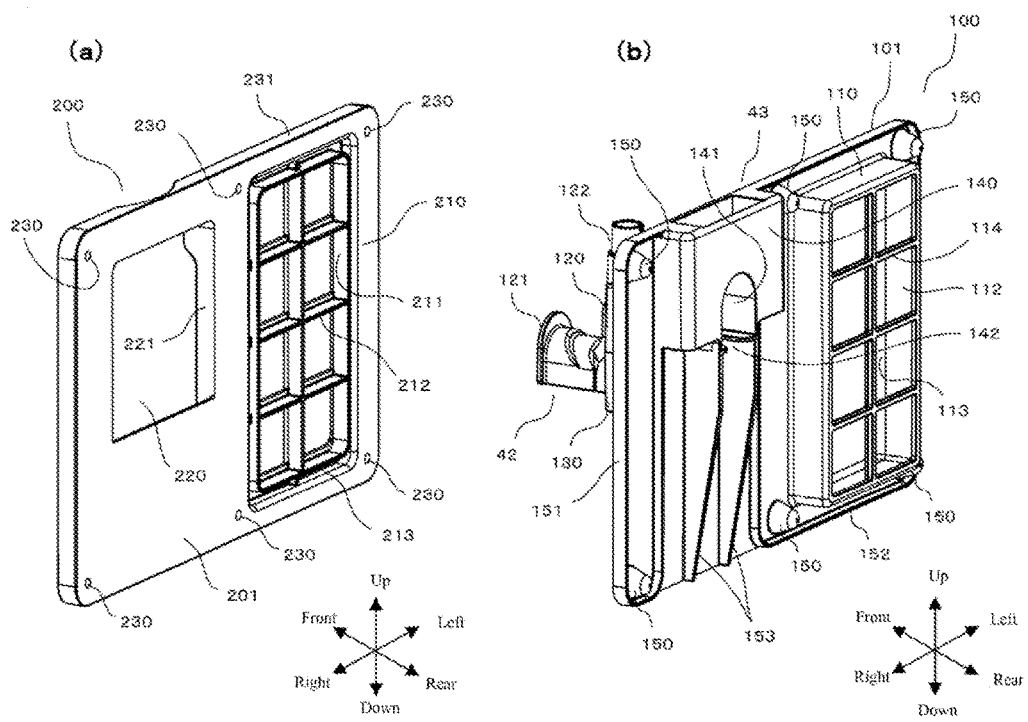
FIG. 8 is a structural diagram illustrating an exhaust and clothes rack retention unit involved in embodiments.
Figure 9:
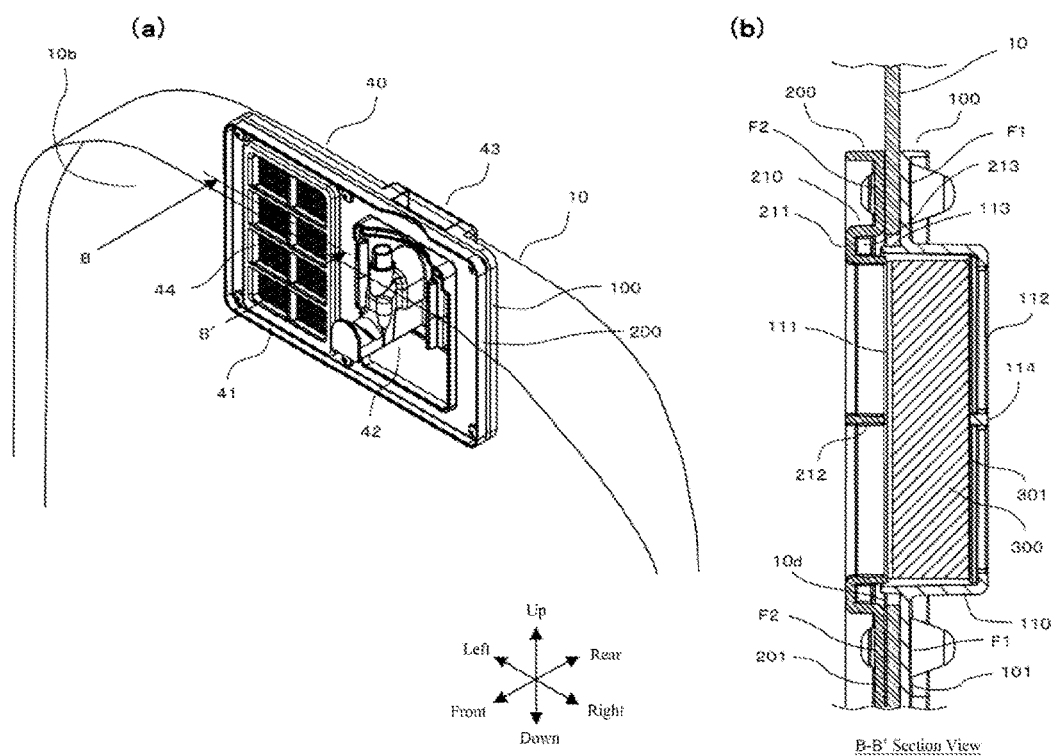
FIG. 9 is a structural diagram illustrating an exhaust and clothes rack retention unit involved in embodiments.

FIG. 7 to FIG. 10 are structural diagrams illustrating an exhaust and clothes rack retention unit 40. FIG. 7 is a three-dimensional diagram illustrating an exploded exhaust and clothes rack retention unit 40 before installed on a bag body 10. FIGS. 8(a) and (b) are respectively rear three-dimensional diagrams illustrating a front unit 200 and a rear unit 100 forming an exhaust and clothes rack retention unit 40. FIG. 9(a) is a three-dimensional diagram illustrating an exhaust and clothes rack retention unit 40 installed on a bag body 10. FIG. 9(b) is a B-B' section view of FIG. 9(a) that an exhaust part 41 is cut off along a horizontal direction. FIGS. 10(a) and (b) are respectively a rear view and a main view illustrating an upper part of a bag body 10. It should be noted that a front surface of the bag body 10 is not shown in FIGS. 7 and 10(b) for convenience, and the bag body 10 is drawn to be transparent in FIG. 9(a).

On the exhaust and clothes rack retention unit 40, the exhaust part 41 is formed at a left half part, and the clothes rack retention part 42 is formed at a front side of a right half part. Moreover, on the exhaust and clothes rack retention unit 40, an installation part 43 for installing the bag body retention part 70 is formed at a rear side of the right half part.

The exhaust and clothes rack retention unit 40 is formed by combining the rear unit 100 and the front unit 200. The rear unit 100 and the front unit 200 are made of material, such as resin material, harder than the material of the bag body 10. The rear unit 100 and the front unit 200 respectively form constituent elements of an exhaust part 41, a clothes rack retention part 42 and an installation part 43 on a lalongate rectangular rear plate 101 and front plate 201. The rear unit 100 and the front unit 200 are respectively equivalent to a first member and a second member of the present disclosure.

The exhaust part 41 includes an exhaust pipe 110 formed on the rear plate 101 and a pipe hood 210 formed on the front plate 201. An ozone removing filter 44 is installed in the exhaust part 41. The exhaust pipe 110 is formed in a manner of protruding backwards, and is rectangular. The front surface of the exhaust pipe 110 as an inlet/outlet 111 of the ozone removing filter 44 is opened, and the rear surface as an air outlet 112 is opened. The circumferential edge of the inlet/outlet 111 is enclosed by a guide frame 113 which protrudes forwards. A lattice 114 is formed at the air outlet 112. The pipe hood 210 is formed in a manner of protruding forwards slightly, and includes a rectangular outer frame 211 and a lattice 212 formed in the outer frame 211. A thickness of the outer frame 211 is greater than a thickness of the lattice 212, and a groove 213 is formed at inner side of the outer frame 211. It should be noted that the guide frame 113 is equivalent to a guide part of the present disclosure.

The ozone removing filter 44 has a rectangular shape with flat front and rear. The ozone removing filter 44 may use, for example, an activated carbon/catalyst filter formed by transferring activated carbon and a catalyst to base material such as aluminum. The ozone removing filter 44 covers periphery of the ozone removing filter 44 through a netty hood 44a in a manner of not being touched by hands. It should be noted that the ozone removing filter 44 may also use other filters with an ozone removing effect, such as a photocatalyst ceramic filter.

The clothes rack retention part 42 includes a first retention part 120 extending from the front surface of the rear plate 101 to the front side and a second retention part 121 formed in front of the first retention part 120. A cylindrical inserting port part 122 which protrudes upwards is formed in the first retention part 120. The second retention part 121 has an upward hook shape.

On the front surface of the rear plate 101, guide bodies 130 are formed on a left side and a right side of the clothes rack retention part 42. In addition, an opening part 220 through which the clothes rack retention part 42 and the left and the right guide bodies 130 penetrate are formed in the front plate 201. A frame body 221 is formed around the opening part 220.

The installation part 43 includes a body part 140 and an installation hole 141. The body part 140 is formed in a square box shape, and protrudes backwards from the rear surface of the rear plate 101. The installation hole 141 is formed in the rear surface of the body part 140, and extends to the inner part of the clothes rack retention part 42 across the rear plate 101. A notch part 142 is formed on the lower surface of the installation hole 141 in a manner of facing the inner part from an opening end of the installation hole 141.

Screw holes 230 through which screws 300 penetrate are formed in the circumferential position of the front plate 201 and in positions of the upper end part and the lower end part of the center of the left-right direction. Moreover, reinforcing ribs 231 which extend all over the entire circumference are formed at an outer circumferential edge of the front surface of the front plate 201.

Installation protrusions 150 for fixing the screws 300 are formed in the circumferential position of the rear plate 101 and in positions of the upper end part and the lower end part of the center of the left-right direction. In addition, on the rear surface of the rear plate 101, a first reinforcing rib 151 which encircles the outer edge part of the rear plate 101 from the right upper end of the body part 140 and connects the right lower end of the body part 140 is formed at the right side of the installation part 43, and a second rib 152 which encircles the outer edge part of the rear plate 101 from the left upper end of the body part 140 and connects the left lower end of the body part 140 is formed at the left side of the installation part 43. Moreover, two third reinforcing ribs 153 which extend from both sides of the installation hole 141 to the lower side are formed on the rear surface of the rear plate 101.

On the upper part of the rear surface of the bag body 10, a first opening part 10d is formed in a position corresponding to the exhaust part 41, and a second opening part 10e is formed in a position corresponding to the clothes rack retention part 42 and the left and the right guide bodies 130. In addition, on the upper part of the rear surface of the bag body 10, insertion holes 10f are formed in positions corresponding to the screw holes 230 of the front plate 201 and the installation protrusions 150 of the rear plate 101.

When the exhaust and clothes rack retention unit 40 is assembled, firstly, the ozone removing filter 44 is accommodated in the exhaust pipe 110 of the rear unit 100. Next, the guide frame 113 is inserted into the first opening part 10d and the left and the right guide bodies 130 are inserted into the second opening part 10e. The rear unit 100 is installed on the upper part of the rear surface of the bag body 10 from outer side of the bag body 10. Next, the front unit 200 is installed on the rear unit 100 from inner side of the bag body 10. Then, the front unit 200 and the rear unit 100 combined by horizontally clamping the upper part of the rear surface of the bag body 10. In this way, as shown in FIG. 9(a), the exhaust and clothes rack retention unit 40 is installed on the upper part of the rear surface of the bag body 10 when being assembled.

Herein, when the rear unit 100 is installed on the rear surface of the bag body 10, the guide frame 113 and the guide bodies 130 are respectively inserted into the first opening part 10d and the second opening part 10e for guidance. Thus, the rear unit 100 becomes easy to be installed on the bag body 10, and the assembly of the exhaust and clothes rack retention unit 40 becomes easy.

In addition, as shown in FIG. 9(b), on the exhaust part 41, the top part of the guide frame 113 of the exhaust pipe 110 is embedded into the groove 213 of the outer frame of the pipe hood 210. Thus, since a sealing effect between the exhaust pipe 110 and the pipe hood 210 is enhanced, the air with ozone, which passes through the exhaust part 41, becomes difficult to leak from the exhaust part 41.

Then, a flat position around the exhaust pipe 110 of the rear plate 101 as a rear flange part F1 covering the circumference of the first opening part 10d from outer side performs a function, a flat position around the pipe hood 210 of the front plate 201 as a front flange part F2 covering the circumference of the first opening part 10d from inner side performs a function. As shown in FIG. 9(b), when the exhaust part 41 is installed on the first opening part 10d, the first opening part 10d is in a state that the circumference is sealed by the rear flange part F1 and the front flange part F2. Thus, the air with the ozone in the bag body 10 becomes difficult to leak from the first opening part 10d. It should be noted that the rear flange part F1 and the front flange part F2 are respectively equivalent to the first flange part and the second flange part of the present disclosure.

Similarly, a flat position around the clothes rack retention part 42 of the rear plate 101 and the left and the right guide bodies 130 as a rear flange part F3 covering the circumference of the second opening part 10e from outer side performs a function, and a flat position around the opening part 220 of the front plate 201 as a front flange part F4 covering the circumference of the second opening part 10e from inner side performs a function. When the clothes rack retention part 42 is installed on the second opening part 10e, the second opening part 10e is in a state that the circumference is sealed by the rear flange part F3 and the front flange part F4. Thus, the air with the ozone in the bag body 10 becomes difficult to leak from the second opening part 10e.

In a state that an exhaust and clothes rack retention unit 40 is installed on an upper part of a rear surface of the bag body 10, as shown in FIG. 10(a), the installation hole 141 of the installation part 43 is located in a center of a left-right direction of the bag body 10. In addition, as shown in FIG. 10(b), the clothes rack retention part 42 is arranged in the bag body 10 and located in a central part of the left-right direction of the bag body 10. A hook of the clothes rack H for clothes to hang the clothes is hooked on the second retention part 121 of the clothes rack retention part 42, and an upper mask 440 is installed at an inserting port part 122 of the first retention part 120. The upper mask 440 is formed in a lalongate platy shape slightly bent into an arch. The upper surface of the bag body 10 is strengthened from inner side through the upper mask 440.

The upper part 10b1 of the rear fabric 10b on the upper part of the rear surface forming the bag body 10 is harder than other parts 10b2 by making a thickness become larger than a thickness of other parts 10b2 of the rear fabric 10b or changing the material of the fabric of other parts 10b2. Thus, the exhaust and clothes rack retention unit 40 can be reliably retained through the upper part of the rear surface of the bag body 10.

Next, the structure of the bag body retention part 70 and the installation structure of the bag body 10 on the bag body retention part 70 are described in detail.

Figure 11:
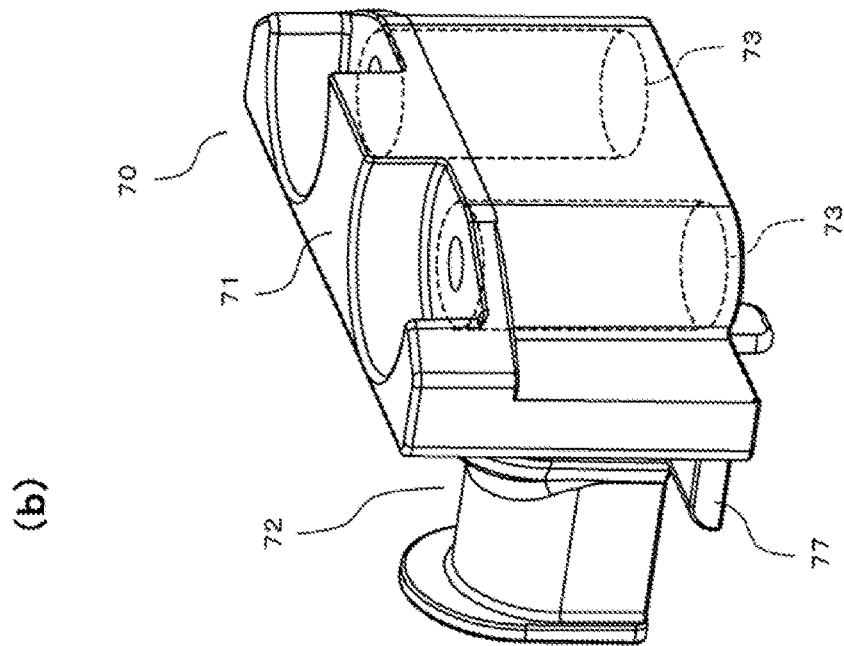
FIG. 11 is a structural diagram illustrating a bag body retention part involved in embodiments.
Figure 11:
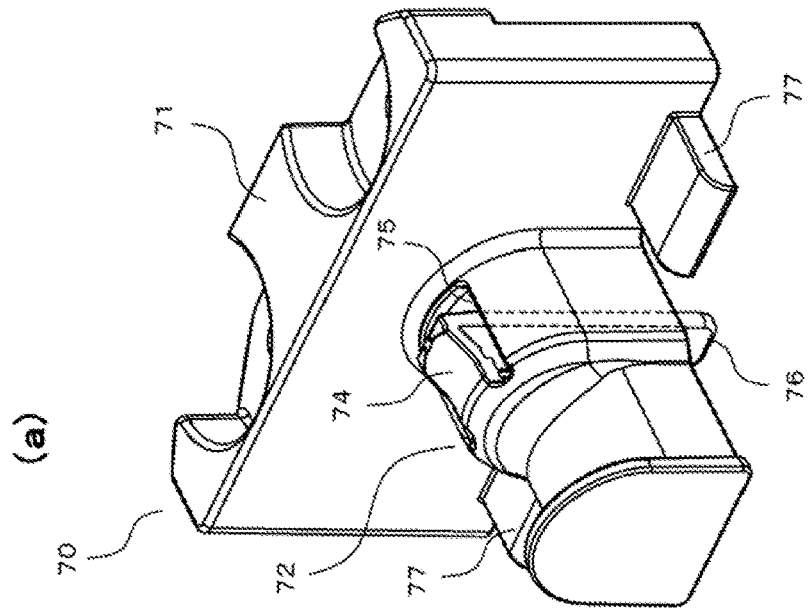
Figure 12:
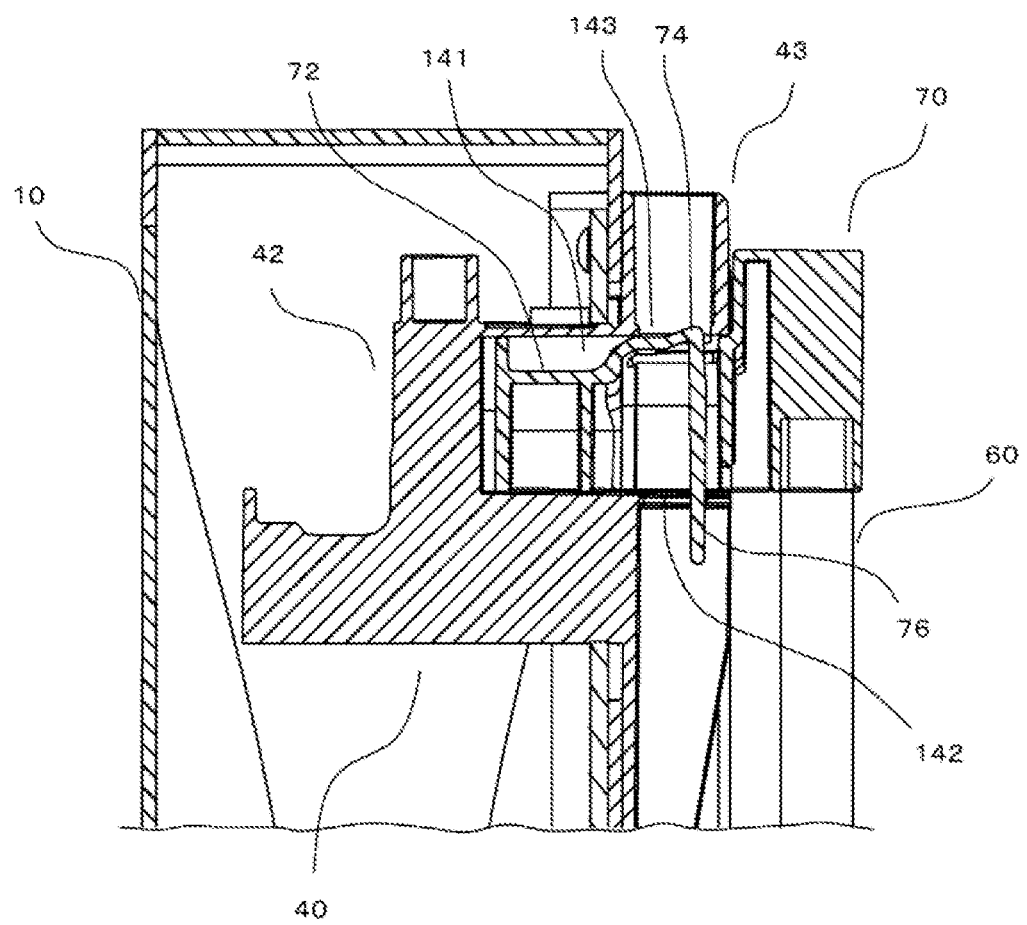
FIG. 12 is a longitudinal section view illustrating a main part in a state that the bag body is installed on a bag body retention part involved in embodiments.

FIG. 11 is a structural diagram illustrating a bag body retention part 70. FIG. 11(a) is a front three-dimensional diagram, and FIG. 11(b) is a rear three-dimensional diagram. FIG. 12 is a longitudinal section view illustrating a main part in a state that the bag body 10 is installed on a bag body retention part 70.

The bag body retention part 70 includes a box-shaped body part 71 and a retention part 72 which extends forwards from the body part 71. Cylindrical insertion holes 73 are formed in a left side and a right side of the body part 71. An upper end part of a rod 61 is inserted into the insertion holes 73.

A clamping claw part 74 is formed on an upper part of a root part of the retention part 72. An opening part 75 is formed around the clamping claw part 74. An inner part of the retention part 72 is made to be hollow, and an operation sheet 76 which droops from the clamping claw part 74 is protruded to the lower part of the retention part 72 from the inner parts of the opening part 75 and the retention part 72. When the operation sheet 76 is pulled to the lower side, the clamping claw part 74 is contracted into the lower side.

The top part of the retention part 72 has an upward hook shape. When the bag body 10 is not installed on the bag body retention part 70, the clothes rack for clothes can be hooked on the top part. At a lower end of the front surface of the body part 71, supporting sheets 77 are formed on the left side and the right side of the retention part 72.

As shown in FIG. 12, under a condition that the bag body 10 is installed on the bag body retention part 70, a user inserts the retention part 72 of the bag body retention part 70 into the installation hole 141 of the exhaust and clothes rack retention unit 40. During insertion, the operation sheet 76 of the retention part 72 passes through the notch part 142 of the installation hole 141. A clamping hole 143 is formed in the upper part of the inlet part of the installation hole 141. When the retention part 72 is inserted into the end of the installation hole 141, the clamping claw part 74 is clamped with the clamping hole 143. Thus, the retention part 72 is not separated from the installation hole 131. The bag body 10 is fixed in a manner of not moving towards the up-down direction and the left-right direction and not separating forwards relative to the bag body retention part 70. In addition, the lower surface of the installation part 43, although not shown in FIG. 12, is supported by a left and a right supporting sheets 77. As shown in FIG. 1(*a*), in a state of being fixed to the bag body retention part 70, the front surface of the bag body 10 faces the front direction of the base 50.

The user pulls the operation sheet 76 to the lower part so that the clamping claw part 74 is contracted and the bag body 10 moves to the front part, thereby removing the bag body 10 from the bag body retention part 70.

Next, a detailed structure of the ozone supply device 20 is described.

Figure 13:
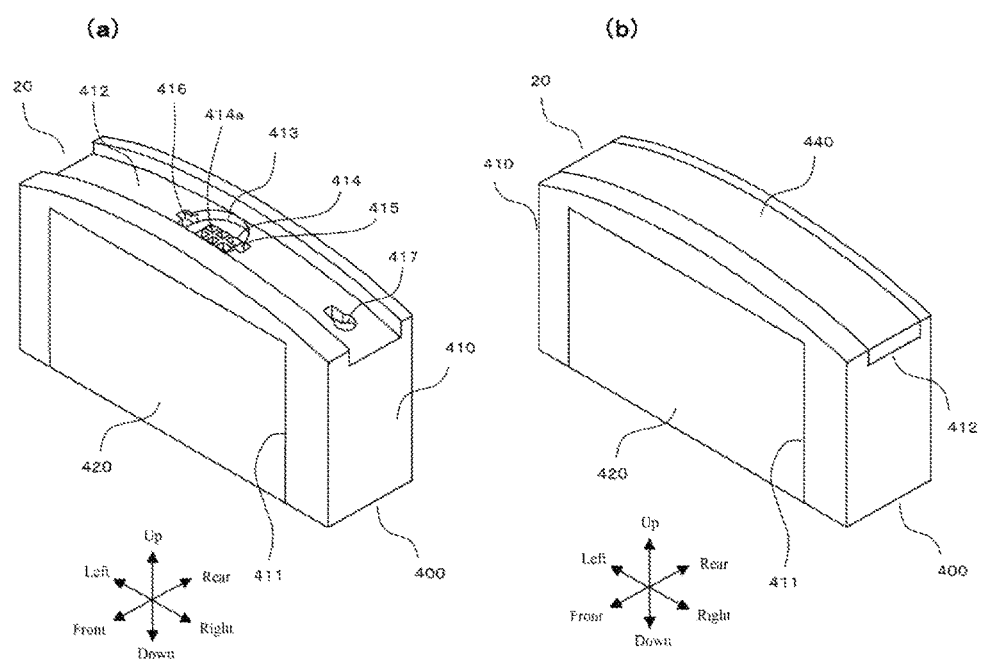
FIG. 13 is a structural diagram illustrating an ozone supply device involved in embodiments.
Figure 14:
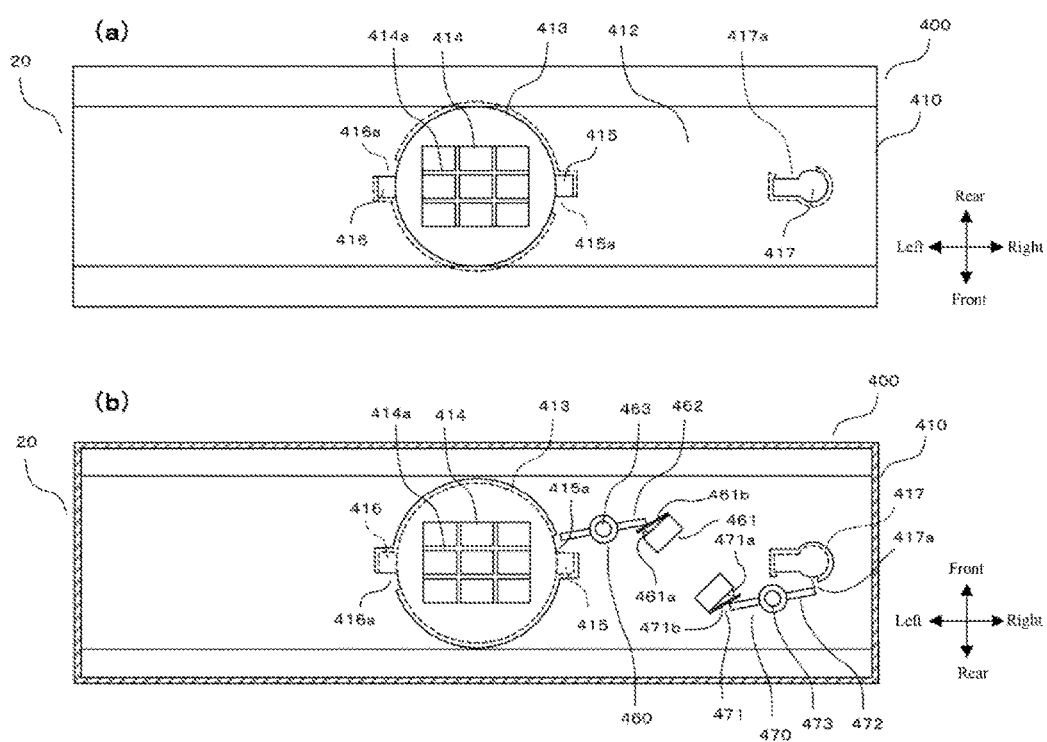
FIG. 14 is a structural diagram illustrating an ozone supply device involved in embodiments.
Figure 15:
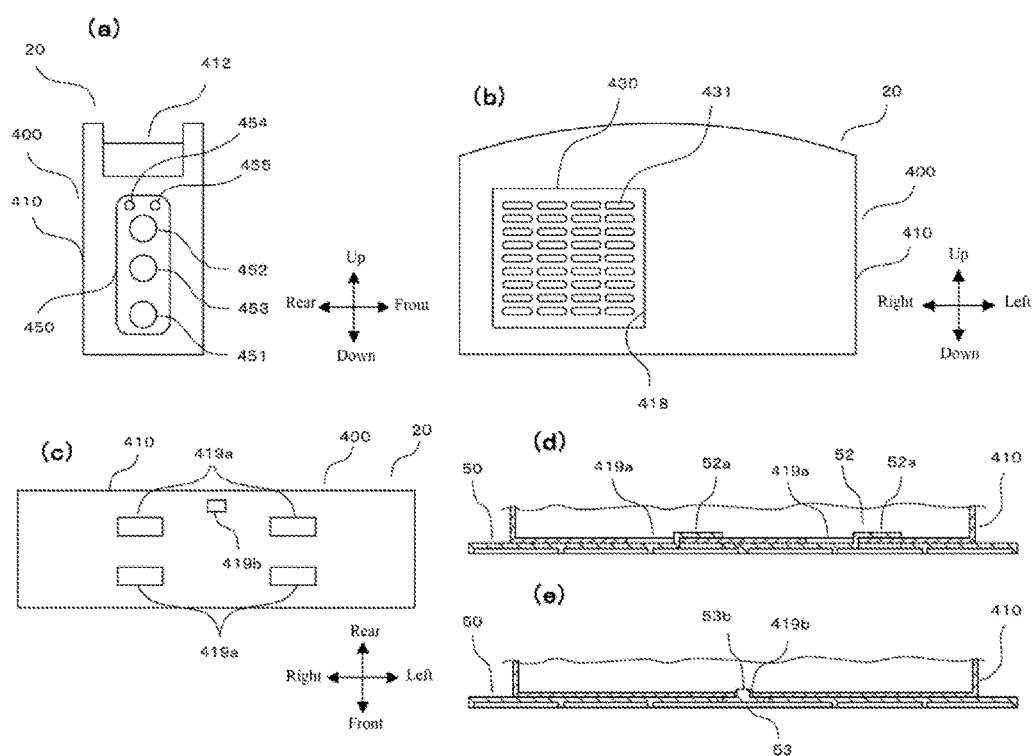
FIG. 15 is a structural diagram illustrating an ozone supply device involved in embodiments.
Figure 16:
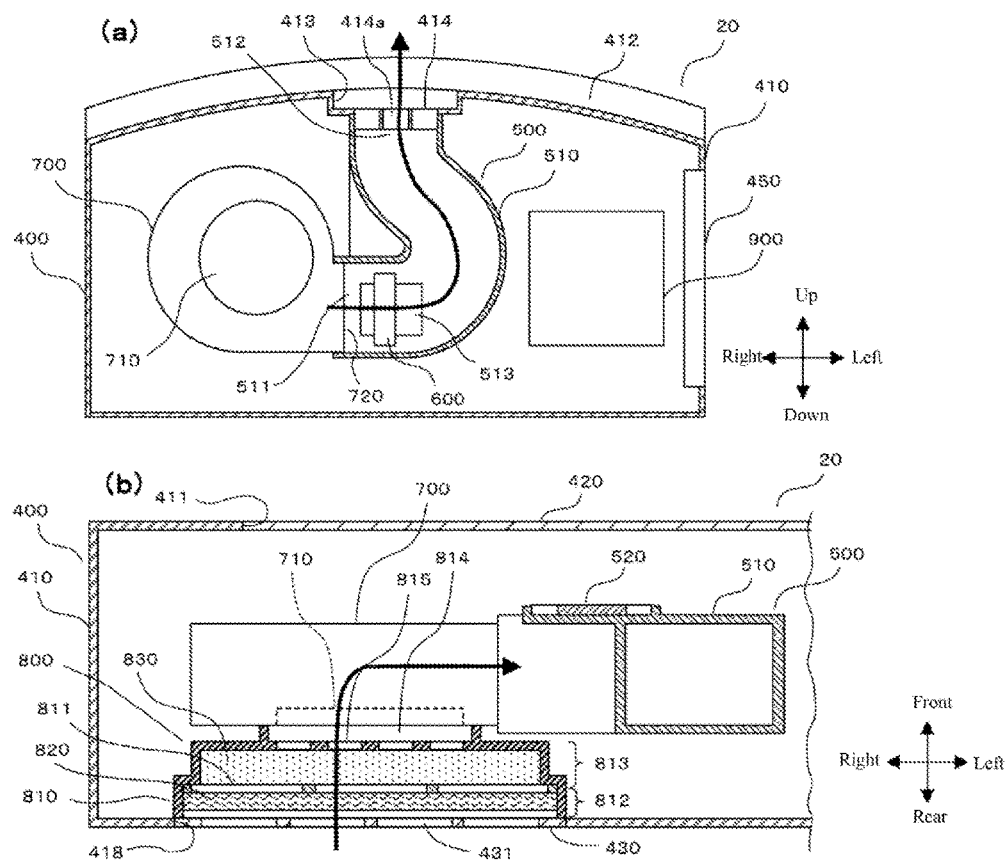
FIG. 16 is a structural diagram illustrating an ozone supply device involved in embodiments.

FIG. 13 to FIG. 16 are structural diagrams illustrating an ozone supply device 20. FIG. 13(*a*) is a three-dimensional diagram illustrating an ozone supply device 20 in a state without installing an upper mask 440. FIG. 13(*b*) is a three-dimensional diagram illustrating an ozone supply device 20 in a state with an upper mask 440. FIG. 14(*a*) is a top view illustrating an ozone supply device 20. FIG. 14(*b*) is a transverse section view for observing an upper surface of a shell 400 of an ozone supply device 20 from inner side. FIGS. 15(*a*) to (*c*) are a left view, a rear view and a bottom view illustrating an ozone supply device 20 respectively. FIGS. 15(*d*) and (*e*) are side section views illustrating a main part of an ozone supply device 20 in a state of being fixed to the base 50. FIG. 16(*a*) is a longitudinal section view for observing an ozone supply device 20 from a rear. FIG. 16(*b*) is a transverse section view for overlooking a main part of an ozone supply device 20. It should be noted that a right inserting concave part 415, a left inserting concave part 416, a lock inserting concave part 417, a pipe detection part 460 and a lock detection part 470 are not shown in FIG. 16(*a*).

The ozone supply device 20 includes a shell 400, a vent pipe 500, an ozone generator 600, a blowing fan 700, an air suction unit 800 and a control unit 900.

The shell 400 includes: a shell body 410, a front mask 420, an air suction hood 430, an upper mask 440 and an operation part 450. As shown in FIG. 13(*a*), the shell body 410 has a lalongate rectangular shape with an upper surface gently bent. A front surface opening part 411 is formed on a front surface of the shell body 410. The front surface opening part 411 is detachable locked through the front mask 420.

On the upper surface of the shell body 410, a concave part 412 sunk into a shape identical with a shape of the upper mask 440 is formed. An inserting port part 413 sunk into a circular shape is arranged in the center of the concave part 412. An exhaust port 414 with a latticed rectification rib 414*a* is formed in the inserting port part 413. At the concave part 412, a right inserting concave part 415 and a left inserting concave part 416 with shapes corresponding to the right claw part 38 and the left claw part 39 of the induction pipe 30 are formed on the left side and the right side of the inserting port part 413. As shown in FIGS. 14(*a*) and (*b*), at a front side of the right inserting concave part 415, a right opening part 415*a* is formed in such a manner that the right claw part 38 inserted into the right inserting concave part 415 only moves to a right turning direction by about an amount of one right claw part 38. Similarly, at a rear side of the left inserting concave part 416, a left opening part 416*a* is formed in such a manner that the left claw part 39 inserted into the left inserting concave part 416 only moves to a right turning direction by about an amount of one left claw part 39.

At the concave part 412, the lock inserting concave part 417 with a shape corresponding to the detection lock 90 is formed at a right end part. As shown in FIGS. 14(*a*) and (b), an opening part 417*a* is formed in a side surface of the rear side of the lock inserting concave part 417.

As shown in FIG. 13(*b*), when the clothes deodorizing device 1 is not used, the upper mask 440 removed from the bag body 10 may be installed on the concave part 412. Thus, since a retention place of the upper mask 440 removed from the bag body 10 is ensured, the upper mask 440 can be prevented from being lost when not used. In addition, dust can be prevented from entering the shell 400 from the exhaust port 414 and the lock inserting concave part 417 when the clothes deodorizing device is not used.

As shown in FIG. 14(*b*), the pipe detection part 460 and the lock detection part 470 are configured at inner side of the upper surface of the shell body 410. The pipe detection part 460 includes a detection switch 461 and a relay rod 462. The detection switch 461 has a switch part 461*a* and a rod part 461*b* for pressing the switch part 461*a*. The relay rod 462 is installed in a free rotation mode on a rotating shaft 463 formed at inner side of the upper surface of the shell body 410. One end is located near the right inserting concave part 415, and the other end comes into contact with the detection switch 461. The lock detection part 470 includes a detection switch 471 and a relay rod 472. The detection switch 471 has a switch part 471*a* and a rod part 471*b* for pressing the switch part 471*a*. The relay rod 472 is installed in a free rotation mode on a rotating shaft 473 formed at inner side of the upper surface of the shell body 410. One end is located near the lock inserting concave part 417, and the other end comes into contact with the detection switch 471.

As shown in FIG. 15(*a*), the operation part 450 is arranged on a left side surface of the shell body 410. The operation part 450 includes a power button 451, a deodorization button 452 and a fragrance increasing button 453. The power button 451 is a button for switching on and switching off a power supply of the clothes deodorizing device 1. The deodorization button 452 is a button for starting deodorization operation. The fragrance increasing button 453 is a button for starting fragrance increasing operation. In addition, the operation part 450 includes a first informing part 454 and a second informing part 455. The first informing part 454 is, for example, composed of LED, and an illuminated lamp is used for informing that the induction pipe 30 is not connected with the ozone supply device 20. The second informing part 455 is, for example, composed of LED, and an illuminated lamp is used for informing that the throwing inlet 11 of the bag body 10 is not locked.

As shown in FIG. 15(b), an air suction port 418 is formed in a rear surface of the shell body 410. The air suction port 418 is detachably locked through the air suction hood 430. A plurality of air suction holes 431 are formed in the air suction hood 430.

As shown in FIG. 15(c), at a bottom surface of the shell body 410, a first installation hole 419a is formed in a position corresponding to each claw part 52a of the first fixing part 52 of the base 50. A second installation hole 419b is formed in a position corresponding to the bulge 53b of the second fixing part 53. After a user presses the pressing part 53c of the second fixing part 53 downwards to contract the bulge 53b, when the claw part 52a loads the ozone supply device 20 on the base 50 through the first installation hole 419a so as to transversely slide the ozone supply device 20, as shown in FIG. 15(d), the claw part 52a is clamped with a bottom surface of the shell body 410. Then, when the user stops pressing the pressing part 53c, as shown in FIG. 15(e), the bulge 53b is embedded into the second installation hole 419b. Thus, the ozone supply device 20 is fixed to the base 50 in a manner of not moving in directions of up and down, front and rear and left and right. Therefore, the ozone supply device 20 can be prevented from falling due to a force applied to the ozone supply device 20 when the bag body 10 is inflated because of the air supplied by the ozone supply device 20.

A vent pipe 500, an ozone generator 600, a blowing fan 700, an air suction unit 800 and a control unit 900 are configured in the shell 400.

As shown in FIGS. 16(a) and (b), the vent pipe 500 includes a pipe body 510 and a pipe cover 520. An induction port 511 of the pipe body 510 is connected with the exhaust port 720 of the blowing fan 700, and an eduction port 512 is connected with the exhaust port 414. The ozone generator 600 is configured near the induction port 511 in the pipe body 510. The pipe body 510 has the following shape: the pipe body 510 extends upwards to the eduction port 512 after bending in a manner of extending from the induction port 511 to the left and beginning to go back to the right over a part of the configuration position of the ozone generator 600. Namely, a part of a downstream side of the pipe body 510 forming the ozone generator 600 crawls in an S shape.

The ozone generator 600 is a discharge type ozone generator. Discharge such as corona discharge, silent discharge and the like is generated between a pair of electrodes, and ozone is generated through the air between a pair of electrodes. At a front surface of the pipe body 510, an opening part 513 is formed in a position corresponding to the ozone generator 600. The opening part 513 is locked through the pipe cover 520. The user may remove the front mask 420 and the pipe cover 520, so as to clean the electrodes through the opening part 513 to maintain the ozone generator 600.

The blowing fan 700 is a centrifugal fan. A suction inlet 710 is arranged in a side surface, and an exhaust port 720 is arranged in a circumferential surface. The suction inlet 710 is opposite to the air suction port 418 on the rear surface of the shell 400. The blowing fan 700 obtains the air from the suction inlet 710, and delivers the obtained air to the ozone generator 600 in the vent pipe 500. The blowing fan 700 may also use other fans besides the centrifugal fan, such as an axial flow fan.

As shown in FIG. 16(b), an air suction unit 800 is arranged between the air suction port 418 of the shell 400 and the suction inlet 710 of the blowing fan 700. The air suction unit 800 includes an air suction pipe 810, a dust filter 820 and an ozone removing filter 830.

The air suction pipe 810 is divided into a first filter accommodating part 812 at a side of the air suction port 418 and a second filter accommodating part 813 at a side of the blowing fan 700 through a latticed dividing plate 811. A dust filter 820 is accommodated at the first filter accommodating part 812, and an ozone removing filter 830 is accommodated at the second filter accommodating part 813. The dust filter 820 removes dust included in the air obtained from the air suction port 418. The ozone removing filter 830 removes the ozone included in the air passing through the dust filter 820. The ozone removing filter 830, identical with the ozone removing filter 44 of the exhaust and clothes rack retention unit 40, may use activated carbon/catalyst filter.

The air suction pipe 810 is provided with a connecting part 814 connected with the suction inlet 710 of the blowing fan 700. The connecting part 814 is connected with the second filter accommodating part 813 through a communication hole 815.

The control unit 900 includes a CPU, a memory and the like to control the ozone generator 600 and the blowing fan 700.

Figure 17:
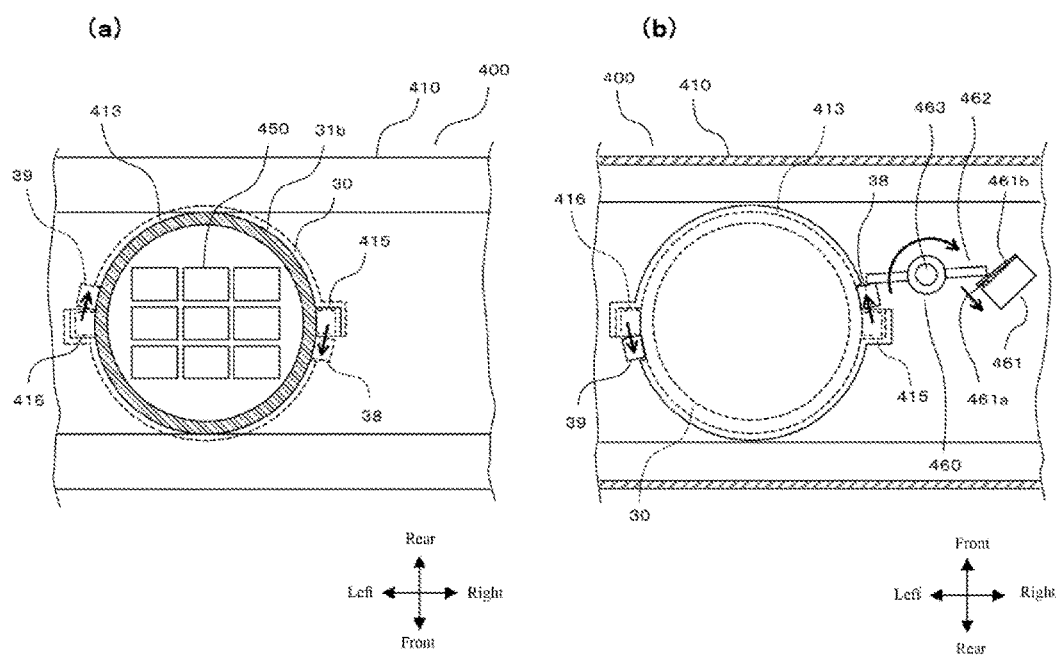
FIG. 17 is a diagram illustrating connection of an induction pipe to an ozone supply device and connection detection through a pipe detection part involved in embodiments.

Next, with reference to FIG. 17, connection of the induction pipe 30 to the ozone supply device 20 and connection detection through the pipe detection part 460 are described.

When the induction pipe 30 is connected with the ozone supply device 20, as shown in FIG. 17(a), the connecting part 31b of the induction pipe 30 is inserted into the inserting port part 413 in a manner of respectively inserting the right claw part 38 and the left claw part 39 into the right inserting concave part 415 and the left inserting concave part 416. Then, when the induction pipe 30 is observed from the upper part and rotates to the right, the right claw part 38 and the left claw part 39 respectively move to inner side of the upper surface of the shell body 410 through the right opening part 415a and the left opening part 416a, and are clamped with the upper surface of the shell body 410. Thus, the induction pipe 30 does not fall to the upper part.

As described in FIG. 6(c), since the right claw part 38 is in a position slightly forward than a center line P of the front-rear direction of the bag body 10, and the left claw part 39 is in a position slightly backward than the center line P of the front-rear direction of the bag body 10, as shown in FIG. 1(a), the induction pipe 30 is connected with the ozone supply device 20 in such a manner that the front surface of the bag body 10 faces the front direction of the ozone supply device 20, i.e., the front direction of the base 50. In addition, as mentioned above, the exhaust and clothes rack retention unit 40 is fixed to the bag body retention art 70 in such a manner that the front surface of the bag body 10 faces the front direction of the base 50. Therefore, the bag body 10 is hanged above the ozone supply device 20 in such a state that the upper part and the lower part are hardly distorted. Thus, the clothes can be well accommodated in the bag body 10, and the air with the ozone can be successfully circulated in the bag body 10.

In this way, the induction pipe 30 is connected with the ozone supply device 20. As shown in FIG. 17(*b*), when the right claw part 38 moves to inner side of the upper surface of the shell body 410, one end side of the relay rod 462 is pressed by the right claw part 38. The relay rod 462 rotates; a rod part 461*b* is pressed by the other end side of the relay rod 462; and a switch part 461*a* is pressed by the pressed rod part 461*b*. Thus, the detection switch 461 detects that the induction pipe 30 is installed on the inserting port part 413.

It should be noted that when the induction pipe 30 is removed from the inserting port part 413, the rod part 461*b* rotates the relay rod 462 through self elasticity, and simultaneously returns to an initial position. Thus, the detection switch 461 detects that the induction pipe 30 is removed from the inserting port part 413.

Figure 18:
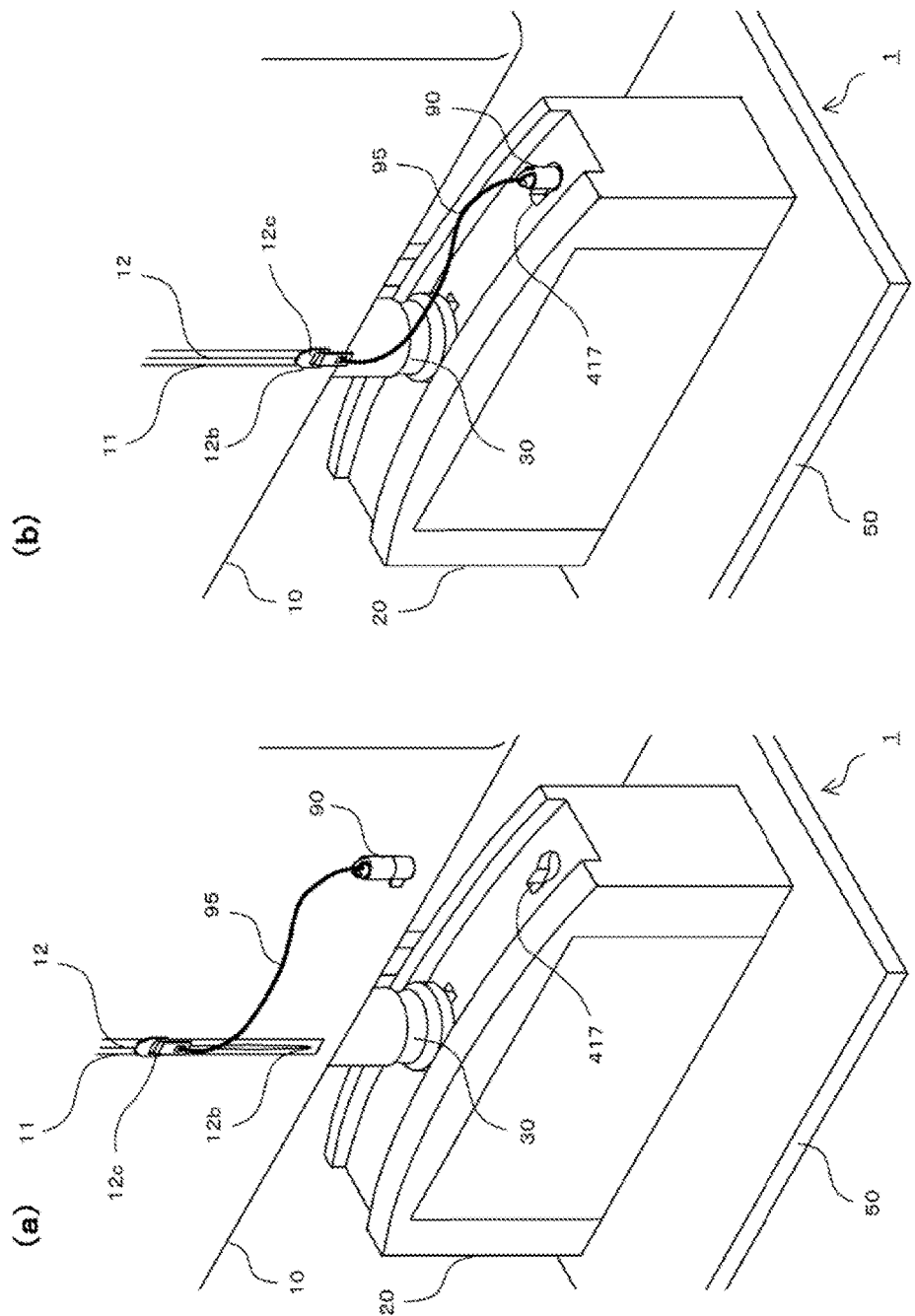
FIG. 18 is a diagram illustrating an action that a lock detection part detects that a throwing inlet of a bag body is locked by a zipper involved in embodiments.
Figure 19:
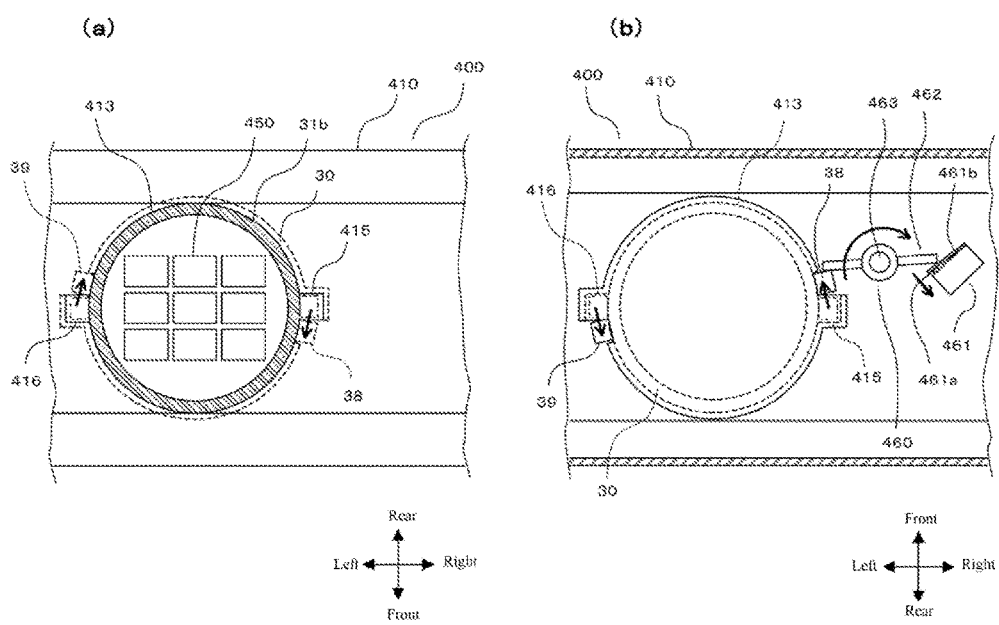
FIG. 19 is a diagram illustrating an action that a lock detection part detects that a throwing inlet of a bag body is locked by a zipper involved in embodiments.

Next, by referring to FIG. 18 to FIG. 19, an action that a lock detection part 470 detects that a throwing inlet 11 of a bag body 10 is locked by a zipper 12 is described.

A connecting rope 95 for connecting the detection lock 90 and the slider 12*c* has a length that the detection lock 90 arrives at the lock inserting concave part 417 when the zipper 12 is locked near the end part 12*b*. Therefore, as shown in FIG. 18(*a*), when the slider 12*c* is not located near the end part 12*b*, the detection lock 90 fails to reach the lock inserting concave part 417 and the user cannot insert the detection lock 90 into the lock inserting concave part 417. Namely, at least in a state that the zipper 12 is completely pulled, the detection lock 90 fails to reach the lock inserting concave part 417. On the other hand, as shown in FIG. 18(*b*), in a state that the zipper 12 is completely closed, the detection lock 90 can reach the lock inserting concave part 417 and the detection lock 90 is inserted into the lock inserting concave part 417.

When the user locks the throwing inlet 11 to the end through the zipper 12, as shown in FIG. 19(*a*), the detection lock 90 is inserted into the lock inserting concave part 417 and the inserted detection lock 90 is observed from the upper part and rotates to the right. As shown in FIG. 19(*b*), the protruding part 91 of the detection lock 90 moves to inner side of the upper surface of the shell body 410 through the opening part 417*a*, and one end side of the relay rod 472 is pressed through the moved protruding part 91. The relay rod 472 rotates; the rod part 471*b* is pressed through the other end side of the relay rod 472; and the switch part 471*a* is pressed by the pressed rod part 471*b*. Thus, the detection switch 471 detects that the detection lock 90 is inserted into the lock inserting concave part 417, i.e., detects that the throwing inlet 11 of the bag body 10 is locked by the zipper 12.

It should be noted that when the detection lock 90 is removed from the lock inserting concave part 417, the rod part 471*b* rotates the relay rod 472 through self elasticity, and simultaneously returns to an initial position. Thus, the detection switch 471 detects that the detection lock 90 is removed from the lock inserting concave part 417.

Next, a detailed structure of the fragrance supply unit 80 is described.

Figure 20:
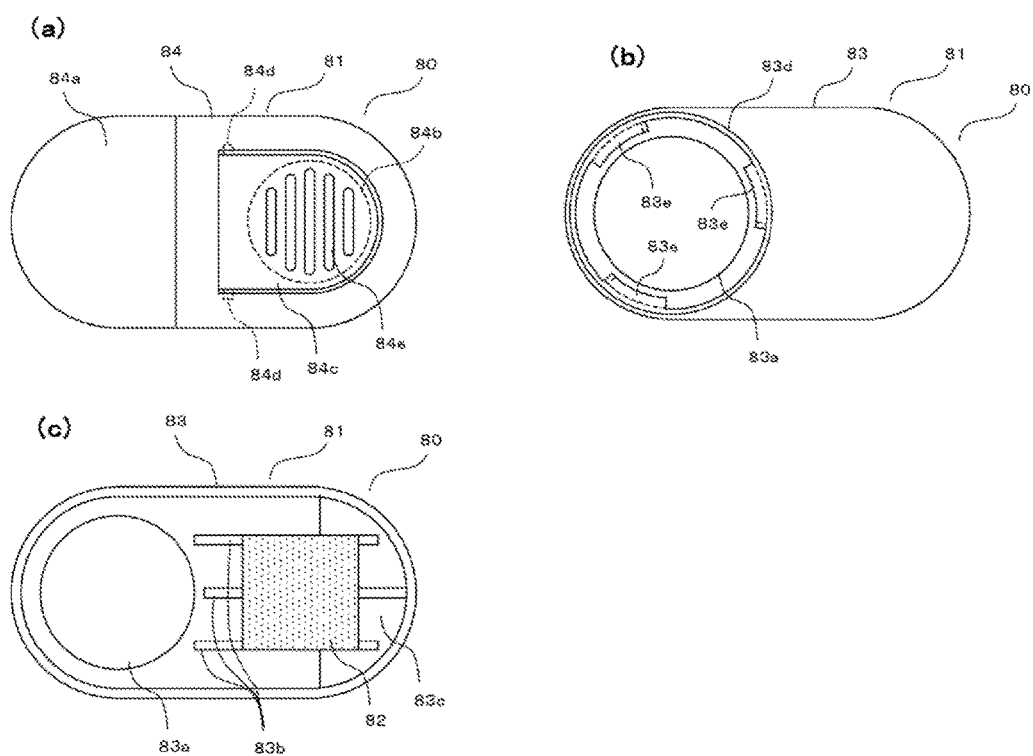
FIG. 20 is a structural diagram illustrating a fragrance supply unit involved in embodiments.
Figure 21:
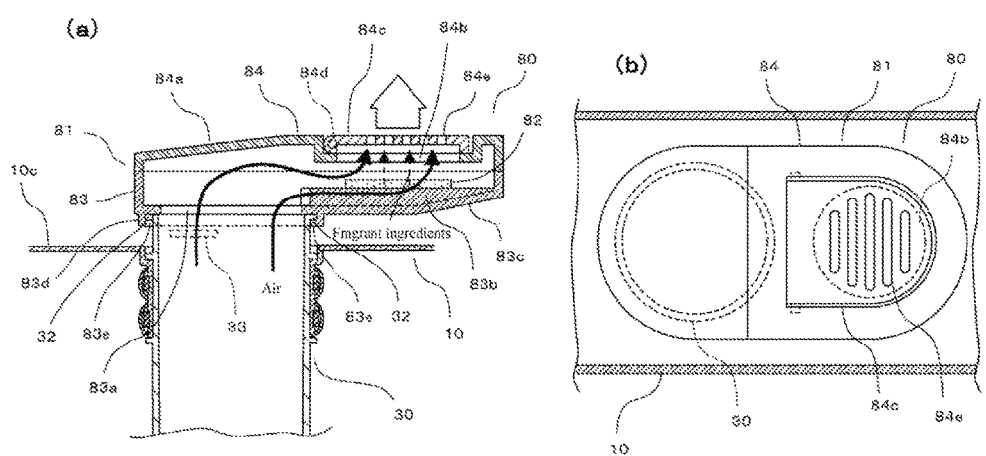
FIG. 21 is a structural diagram illustrating a fragrance supply unit involved in embodiments.

FIG. 20 and FIG. 21 are structural diagrams illustrating a fragrance supply unit 80. FIGS. 20(*a*) and (*b*) are a top view and a bottom view illustrating a fragrance supply unit 80 respectively. FIG. 20(*c*) is a top view illustrating a fragrance supply unit 80 in a state that an upper box body 84 is removed. FIG. 21 is a longitudinal section view illustrating a central part of a lower part of a bag body 10 in a state that a fragrance supply unit 80 is installed on an induction pipe 30. FIG. 21(*b*) is a transverse section view illustrating a central part of a lower part of a bag body 10 in a state that a fragrance supply unit 80 is installed on an induction pipe 30.

The fragrance supply unit 80 includes an accommodating box 81 which has an oval box shape when overlooked, and a fragrant body 82 accommodated in the accommodating box 81. The accommodating box 81 includes a lower box body 83 with an opened upper surface and an upper box body 84 with an opened bottom surface.

At the bottom surface of the lower box body 83, an air suction port 83*a* is formed at one end side of a long edge direction, and a plurality of ribs 83*b* adjacent to the air suction port 83*a* and extending to the long edge direction are formed. The fragrant body 82 is loaded above the plurality of ribs 83*b*. In addition, on the other end side, the bottom surface of the lower box body 83 has an inclined surface 83*c* which becomes higher to the other end side. Moreover, at the bottom surface of the lower box body 83, a cylindrical connecting port 83*d* is formed in a manner of encircling the air suction port 83*a*. Claw parts 83*e* are formed in positions of the connecting port 83*d* corresponding to the clamping pieces 32 of the introduction pipe 30.

The upper box body 84 is installed on the upper surface of the lower box body 83. The upper surface of the upper box body 84 has an inclined surface 84*a* which becomes higher to the other end in a position opposite to the air suction port 83*a*. In addition, an opening part 84*b* is formed in a position opposite to a plurality of ribs 83*b* on the upper surface of the upper box body 84. The opening part 84*b* is covered by a cover part 84*c* in an openable and closable manner. The cover part 84*c* rotates by taking a hinging part 84*d* as a center. A plurality of slit-shaped vent holes 84*e* are formed in the cover part 84*c*.

The fragrant body 82 is formed by porous material and the like which may be immersed in a liquid flavoring agent. The user opens the cover part 84*c* and arranges the fragrant body 82 into the accommodating box 81 from the opening part 84*b*.

When the fragrance supply unit 80 is installed on the induction pipe 30, the connecting port 83*d* is inserted into the top part of the introduction pipe 30 in a state that the claw parts 83*e* and the clamping pieces 32 are staggered in positions. Then, the fragrance supply unit 80 rotates to overlapping positions of the claw parts 83*e* and the clamping pieces 32. As shown in FIG. 21(*a*), the clamping pieces 32 and the claw parts 83*e* are clamped and the fragrance supply unit 80 does not fall upwards. It should be noted that through existence of the front flange part 33 and the rear flange part 34, the side fabric 10*c* of the lower surface of the bag body 10 can be prevented from being engaged between the connecting port 83*d* and the introduction pipe 30.

As shown in FIG. 21(*b*), in a state that the fragrance supply unit 80 is installed on the induction pipe 30, the fragrance supply unit 80 is configured in the bag body 10 in such a manner that a long edge direction of the fragrance supply unit 80 forms a left-right direction of the bag body 10. As mentioned above, since the introduction pipe 30 is fixed to the cylindrical part 15 in a manner of not rotating relative to the bag body 10, the fragrance supply unit 80 correctly installed on the introduction pipe 30 does not come into contact with the front surface and the rear surface of the bag body 10.

Next, deodorization operation and fragrance increasing operation performed on the clothes deodorizing device 1 are described.

Figure 10:
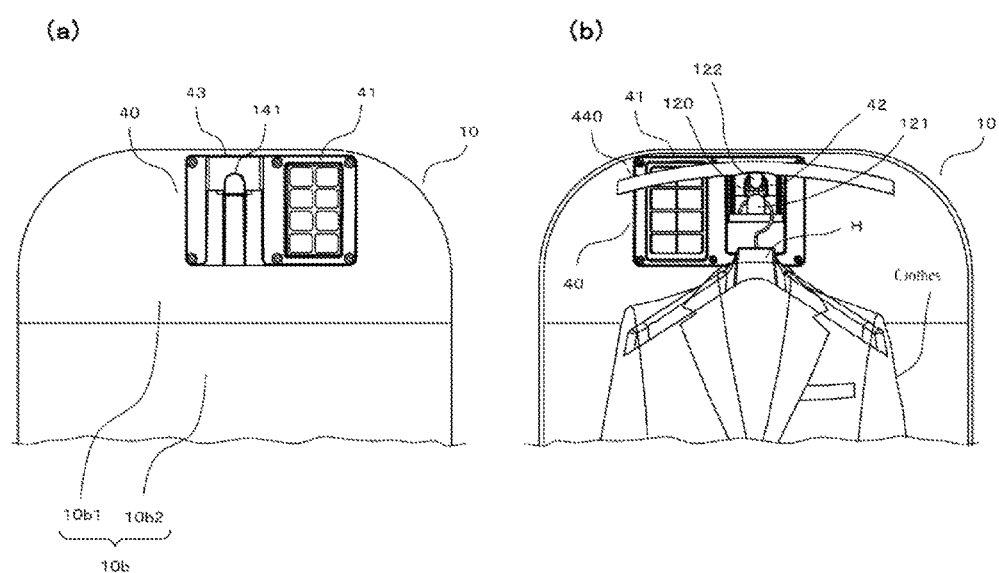
FIG. 10 is a structural diagram illustrating an exhaust and clothes rack retention unit involved in embodiments.

Under a condition of performing deodorization operation, the user accommodates the clothes hanged on the clothes rack H for clothes into the bag body 10 hanged on the bag body retention part 70. At this moment, as shown in FIG. 10(*b*), the user hangs the clothes in the bag body 10 to the second retention part 121 of the clothes rack retention part 42 with the clothes rack H. In this way, in the bag body 10, the clothes are hanged through the clothes rack retention part 42. The user presses the deodorization button 452 of the operation part 450. When the pipe detection switch 460 detects that the induction pipe 30 is installed on the ozone supply device 20, and the lock detection part 470 detects that the lock 90 is inserted into the lock inserting concave part 417, i.e., when a condition that the throwing inlet 11 of the bag body 10 is locked by the zipper 12 is detected, the control unit 900 starts the deodorization operation to enable the blowing fan 700 and the ozone generator 600 to operate. When the induction pipe 30 is not installed on the ozone supply device 20, the control unit 900 does not start the deodorization operation and enables the first informing part 454 to illuminate a lamp. In addition, when the throwing inlet 11 is not locked, the control unit 900 does not start the deodorization operation and enables the second informing part 455 to illuminate a lamp.

When the deodorization operation is started, outside air is taken into the air suction pipe 810 from the air suction port 418 to remove dust and ozone included in the air through the dust filter 820 and the ozone removing filter 830 in the air suction pipe 810. The air without dust and ozone is delivered into the vent pipe 500 through the blowing fan 700 (with reference to an arrow in FIG. 16(*b*)). The air flowing in the vent pipe 500 is mixed with the ozone generated by the ozone generator 600 when passing through the ozone generator 600. In this way, air with the ozone arrives at the exhaust port 414 through the vent pipe 500 and is exhausted from the exhaust port 414 (with reference to an arrow in FIG. 16(*a*)).

The air exhausted from the ozone supply device 20 and including the ozone is guided into the bag body 10 through the induction pipe 30. As shown by an arrow in FIG. 1(*a*), the air guided into the bag body 10 and including the ozone is in contact with the clothes in the bag body 10 from bottom to top and simultaneously flows. The clothes are deodorized through a deodorization effect of the ozone included in the air. Herein, although the lower part of the clothes is opened greatly, since the air with the ozone flows from bottom to top in the bag body 10, the air is easy to spread over the inner part of the clothes. Thus, comprehensive deodorization can be performed on outer side and inner side of the clothes.

In addition, by hanging the bag body 10 to the bag body retention part 70, the clothes are hanged on the clothes rack H for clothes, thereby ensuring a clearance between the upper part of the bag body 10 and a shoulder part of the clothes. Thus, since the ozone is also easy to spread over the shoulder part of the clothes, a deodorization effect can be enhanced.

The air with a reduced ozone concentration through deodorization for the clothes, as shown by a dotted arrow in FIG. 1(*a*), is exhausted from the bag body 10 through the exhaust part 41 above the bag body 10. Ozone is removed from deodorized air through the ozone removing filter 44 when the deodorized air passes through the exhaust part 41. Thus, the concentration of the ozone in the air exhausted from the bag body 10 is further reduced.

Next, under a condition of performing fragrance increasing operation, the user accommodates the clothes into the bag body 10 hanged on the bag body retention part 70, and as shown in FIG. 21, in the bag body 10, the fragrance supply unit 80 provided with the fragrant body 82 is installed on the induction pipe 30. The user presses the fragrance increasing button 453 of the operation part 450. When the pipe detection switch 460 detects that the induction pipe 30 is installed on the ozone supply device 20, and when the lock detection part 470 detects that the throwing inlet 11 of the bag body 10 is locked by the zipper 12, the control unit 900 starts the fragrance increasing operation and enables the blowing fan 700 to operate. When the induction pipe 30 is not installed on the ozone supply device 20, the control unit 900 does not start the fragrance increasing operation and enables the first informing part 454 to illuminate a lamp. In addition, when the throwing inlet 11 is not locked, the control unit 900 does not start the fragrance increasing operation and enables the second informing part 455 to illuminate a lamp.

When the fragrance increasing operation is started, as shown in FIG. 21(*a*), the air exhausted from the induction pipe 30 is introduced into the accommodating box 81 from the air suction port 83*a*. The introduced air flows upwards after flowing towards the other end side along a plurality of ribs 83*b*. Through the air that passes through the fragrant body 82, fragrant ingredients included in the fragrant body 82 volatilize, and are mixed into the air. The air with the fragrant ingredients is exhausted into the bag body 10 through the opening part 84*b* and the vent hole 84*e*. It should be noted that the air successfully flows in the accommodating box 81 through two inclined surfaces 83*c* and 84*a*, arranged on the accommodating box 81.

Similar to the condition of the deodorization operation, the air with the fragrant ingredients flows from bottom to top in the bag body 10. In addition, since air pressure in the bag body 10 is increased, a fragrance increasing effect of the clothes can be enhanced.

Effects of Present Embodiment

The following effect can be performed above through the present embodiment.

(1) Since the clothes deodorizing device 1 adopts such a structure that the air with the ozone is supplied from the ozone supply device 20 and the air with the fragrant ingredients is supplied to the bag body 10 for accommodating the clothes to perform deodorization and fragrance increasing operation of the clothes, clothes deodorizing device 1 can be easily arranged in a family without a large arrangement space.

(2) Since the exhaust part 41 with the ozone removing filter 44 is arranged on the bag body 10, the ozone in the air is removed by the ozone removing filter 44 when the air beneficial for clothes deodorization is exhausted through the exhaust part 41. Thus, the air after the ozone concentration is reduced can be exhausted from the bag body 10.

(3) Since the exhaust part 41 is formed separately from the bag body 10 by material harder than material of forming the bag body 10, the ozone removing filter 44 can be stably kept in the exhaust part 41.

(4) When the exhaust part 41 is installed on the first opening part 10*d*, the circumference of the first opening part 10*d* is sealed by the rear flange part F1 and the front flange part F2. Thus, the air with the ozone in the bag body 10 is difficult to leak from the first opening part 10*d*.

(5) When the rear unit 100 is installed on the rear surface of the bag body 10, the guide frame 113 as a guide part is inserted into the first opening part 10*d*. Thus, the rear unit 100 is easy to be installed on the bag body 10, and the assembly of the exhaust and clothes rack retention unit 40 becomes easy.

(6) Since the clothes rack retention part 42 and the installation part 43 are formed integrally with the exhaust part 41, the exhaust part 41, the clothes rack retention part 42 and the installation part 43 are installed on the bag body 10 in one step.

Change Embodiment

Although embodiments regarding the present disclosure are described above, the present disclosure is not limited to the above-mentioned embodiments. In addition, various changes except for the above may further be made to embodiments of the present disclosure.

For example, in above embodiments, the exhaust pipe 110 is formed on the rear unit 100, and the pipe hood 210 is formed on the front unit 200. However, the exhaust pipe 110 may be formed on the front unit 200, and the pipe hood 210 may be formed on the rear unit 100. In this case, the guide frame 113 is formed on the front unit 200, and the groove 213 is formed on the rear unit 100.

In addition, in above embodiments, the clothes rack retention part 42 and the installation part 43 are formed integrally with the exhaust part 41. However, the clothes rack retention part 42 and the installation part 43 may also be formed separately from the exhaust part 41. In this case, the exhaust part 41 is also composed of the rear unit having the rear flange part around the exhaust pipe 110 and the front unit having the front flange part around the pipe hood 210. Similarly, the clothes rack retention part 42 and the installation part 43 are composed of the rear unit having the rear flange part around the clothes rack retention part 42 and the left and the right guide part bodies 130 and the front unit having the front flange part around the opening part 220.

Then, in above embodiments, the exhaust parts 41 are arranged on the side surfaces of the clothes rack retention part 42 and the installation part 43. However, the exhaust parts 41 may be arranged above the clothes rack retention part 42 and the installation part 43. In addition, one ozone removing filter 44 may be arranged or a plurality of ozone removing filters 44 may be arranged in a stacked mode.

In addition, various changes may be properly made to embodiments of the present disclosure within a scope of technical concepts shown in a scope of claims.

LIST OF REFERENCE NUMERALS

10: Bag body; 20: Ozone supply device; 40: Exhaust and clothes rack retention unit; 41: Exhaust part; 42: Clothes rack retention part; 43: Installation part; 44: Ozone removing filter; 70: Bag body retention part; 100: Rear unit (first member); 110: Exhaust pipe; 113: Guide frame (guide part); 200: Front unit (second member); 210: Pipe hood; F1: Rear flange part (first flange part); F2: Front flange part (second flange part).

What is claimed is:

1. A clothes treating device, comprising:
a bag body for accommodating clothes;
an ozone supply device to supply air with ozone into the bag body;
an exhaust part arranged on the bag body and used for air exhausted outside the bag body to pass through, the exhaust part installed on an opening part formed in the bag body, the exhaust part composed of a first member installed on the opening part from an outer side of the bag body and a second member installed on the opening part from an inner side of the bag body, the first member having a first flange part covering a periphery of the opening part from the outer side, and the second member having a second flange part covering the periphery of the opening part from the inner side, the exhaust part assembled by combining the first member and the second member in a manner of clamping the bag body from the inner side and the outer side;
a bag body retention part for retaining the bag body above the ozone supply device;
an installation part installed on the bag body retention part, the installation part integrally formed with the exhaust part; and
an ozone removing filter arranged on the exhaust part and used for removing ozone in air passing through the exhaust part.

2. The clothes treating device according to claim 1, wherein a guide part, which is to be inserted into the opening part when one member of the first member and the second member is installed on the opening part, is formed on the one member of the first member and the second member.

3. The clothes treating device according to claim 1, wherein a clothes rack retention part, for retaining a clothes rack for clothes to hang clothes in the bag body, is integrally formed with the exhaust part.

4. The clothes treating device according to claim 2, wherein a clothes rack retention part, for retaining a clothes rack for clothes to hang clothes in the bag body, is integrally formed with the exhaust part.

* * * * *